US005723127A

United States Patent [19]
Scott et al.

[11] Patent Number: 5,723,127
[45] Date of Patent: Mar. 3, 1998

[54] COMPOSITIONS AND METHODS FOR USE OF IL-12 AS AN ADJUVANT

[75] Inventors: Phillip Scott, Swarthmore; Giorgio Trinchieri, Wynnewood, both of Pa.

[73] Assignees: The Trustees of the University of Pennsylvania; The Wistar Institute of Anatomy & Biology, both of Philadelphia, Pa.

[21] Appl. No.: 621,493

[22] Filed: Mar. 25, 1996

Related U.S. Application Data

[60] Division of Ser. No. 265,087, Jun. 17, 1994, Pat. No. 5,571,515, which is a continuation-in-part of Ser. No. 229,282, Apr. 18, 1994, abandoned.

[51] Int. Cl.⁶ .......................... A61K 39/00; A61K 39/12; A61K 39/005; C07K 1/00
[52] U.S. Cl. ............................ 424/184.1; 424/191.1; 424/204.1; 424/234.1; 424/269.1; 530/350
[58] Field of Search ........................ 424/184.1, 191.1, 424/204.1, 234.1, 269.1

[56] References Cited

FOREIGN PATENT DOCUMENTS

| 609739 | 8/1994 | European Pat. Off. . |
|---|---|---|
| 3922444 | 1/1991 | Germany . |
| WO90/05147 | 5/1990 | WIPO . |
| WO94/01139 | 1/1994 | WIPO . |

OTHER PUBLICATIONS

T. Mosmann et al., "Two Types of Murine Helper T Cell Clone", *J. Immunol.*, 136(7):2348–2357 (Apr. 1, 1986).
H. Warren et al., "Current Status of Immunological Adjuvants", *Ann. Rev. Immunol.*, 4:369–388 (Apr., 1986).
A. D'Andrea et al., "Production of Natural Killer Cell Stimulatory Factor (Interleukin 12) by Peripheral Blood Mononuclear Cells", *J. Exp. Med.*, 176:1387–1398 (Nov., 1992).
M. Kobayashi et al., "Identification and Purification of Natural Killer Cell Stimulatory Factor (NKSF), a Cytokine with Multiple Biologic Effects on Human Lymphocytes", *J. Exp. Med.*, 170:827–845 (Sep., 1989).
S. Chan et al., "Induction of Interferon gamma Production by Natural Killer Cell Stimulatory Factor: Characterization of the Responder Cells and Synergy with Other Inducers", *J. Exp. Med.*, 173:869–879 (Apr., 1991).
F. Heinzel et al., "Recombinant Interleukin 12 Cures Mice Infected with Leishmania Major", *J. Exp. Med.*, 177:1505–1509 (May, 1993).
J. Sypek et al., "Resolution of Cutaneous Leishmaniasis:Interleukin 12 Initiates a Protective T Helper Type 1 Immune Response", *J. Exp. Med.*, 177:1797–1802 (Jun., 1993).
A. McKnight et al., "Effects of IL-12 on Helper T Cell-Dependent Immune Responses in vivo", *J. Immunol.*, 152:2172–2179 (Jun., 1994).
L. Afonso et al., "The Adjuvant Effect of Interleukin-12 in a Vaccine Against Leishmania Major", *Science*, 263:235–237 (Jan. 14, 1994).

C-S. Hsieh et al., "Development of TH1 CD4+ T Cells Through IL-12 Produced by Listeria-Induced Macrophages", *Science*, 260:547–549 (Apr. 23, 1993).
P. Scott, "IL-12: Initiation Cytokine for Cell-Mediated Immunity", *Science*, 260:496–497 (Apr. 23, 1993).
R. Manetti et al., "Natural Killer Cell Stimulatory Factor (Interleukin 12 [IL-12]) Induces T Helper Type 1 (Th1) — Specific Immune Responses and Inhibits the Development of IL-4-Producing Th Cells", *J. Exp. Med.*, 177:1199–1204 (Apr. 1993).
G. Freeman et al., "B7, a New Member of the Ig Superfamily with Unique Expression on Activated and Neoplastic B Cells", *J. Immunol.*, 143 (8):2714–2722 (Oct. 15, 1989).
K. Jerome et al., "Tumor-Specific Cytotoxic T Cell Clones from Patients with Breast and Pancreatic Adenocarcinoma Recognize EBV-Immortalized B Cells Transfected with Polymorphic Epithelial Mucin Complementary DNA", *J. Immunol.*, 151)3):1654–1662 (Aug. 1, 1993).
R. Kurth et al., "The Quest for an AIDS Vaccine: The State of the Art and Current Challenges", *AIDS Research and Human Retroviruses*, 7(5):425–433 (1991).
G. Butcher, "Mechanisms of Immunity to Malaria and the Possibilities of a Blood-Stage Vaccine: A Critical Appraisal", *Parasitology*, 98:315–327 (1989).
W. Greene, "AIDS and the Immune System, the AIDS Virus Exploits the Immune System to Replicate Itself. New Findings are Showing how it Wreaks Havoc on the Body's Defenses", *Scientific American*, pp. 99–105 (Sep., 1993).
D. Hentges, "Medical Microbiology, A Review with Questions and Explanations", pp. 14–18, 25–29, 206–209, 286–287 (1986).
T Wynn et al., "Endogenous Interleukin 12 (IL-12) Regulates Granuloma Formation Induced by Eggs of Schistosoma mansoni and Exogenous IL-12 Both Inhibits and Prophylactically Immunizes Against Egg Pathology", *J. Exp. Med.*, 179:1551–1561 (May, 1994) [Wynn I ].
T. Wynn et al., "An IL-12-based Vaccination Method for Preventing Fibrosis Induced by Schistosome Infection", *Nature*, 376:594–596 (Aug. 17, 1995) [Wynn II ].
T. Wynn et al., "IL-12 Enhances Vaccine-Induced Immunity to Schistosoma mansoni in Mice and Decreases T Helper 2 Cytokine Expression, IGE Production, and Tissue Eosinophilia", *J. Immunol.*, 154:4701–4709 (1995) [Wynn III ].

(List continued on next page.)

Primary Examiner—Lynette F. Smith
Attorney, Agent, or Firm—Howson and Howson

[57] ABSTRACT

Improved vaccine compositions and methods of making same are provided, which vaccines are characterized by an antigen from a pathogen and an effective adjuvanting amount of Interleukin-12. These IL-12 adjuvanted vaccines are capable of increasing the vaccinated host's cell mediated immune response to provide an increased and protective immune response to the pathogen. Also disclosed are methods for vaccinating hosts by administering a vaccine containing an antigen from a pathogenic microorganism and co-administering an adjuvanting amount of IL-12. Vaccines or therapeutic compositions directed against a cancer may also be adjuvanted with IL-12 according to this invention.

8 Claims, 7 Drawing Sheets

OTHER PUBLICATIONS

T. Wynn et al, "IL12 as an Adjuvant for Vaccines Designed to Prevent Infection and Immunopathology by Schistosomes", *Res. Immunol.,* 146:582–590 (1995) [Wynn IV ].

T. Germann et al, "The INfluence of IL12 on the Development of Th1 and Th2 Cells and its Adjuvant Effect for Humoral Immune Responses", *Res. Immunol.,* 146:481–485 (1995).

M. Miller et al, "Nonviable Bacterial Antigens Administered with IL–12 Generate Antigen–Specific T Cell Responses and Protective Immunity Against Listeria monocytogenes", *J. Immunol.,* 155:4817–4828 (1995).

Y. Noguchi et al, "Influence of Interleukin 12 on p53 Peptide Vaccination Against Established Meth A Sarcoma", *Proc. Natl. Acad. Sci. USA,* 92:2219–2223 (Mar., 1995).

Y-W. Tang et al, "Interleukin–12 Treatment During Immunization Elicits a T Helper Cell Type 1–like Immune Response in Mice Challenged with Respiratory Syncytcal Viral and Improves Vaccine Immunogenicity", *J. Infect. Dis.,* 172:734–738 (Sep., 1995).

S. Wolf et al, "Activity of IL12 as Adjuvant in Promoting Th1 and Th2 Recall Responses", *Res. Immunol.,* 146:486–493 (1995).

J. Bliss et al, "IL–12, as an Adjuvant, Promotes a T Helper 1 Cell, but does not Suppress a T Helper 2 Cell Recall Response", *J. Immunol.,* 156:887–894 (1996).

J. Rao et al, "IL–12 is an Effective Adjuvant to Recombinant Vaccinia Virus–Based Tumor Vaccines", *J. Immunol.,* 156:3357–3365 (1996).

M. Vagliani et al, "Interleukin 12 Potentiates the Curative Effect of a Vaccine Based on Interleukin 2–transduced Tumor Cells", *Cancer Research,* 56:467–470 (Feb. 1, 1996).

M. Rodolfo et al, "Immunotherapy of Experimental Metastases by Vaccination with Interleukin Gene–Transduced Adenocarcinoma Cells Sharing Tumor–Associated Antigens", *J. Immunol.,* 157:5536–5542 (1996).

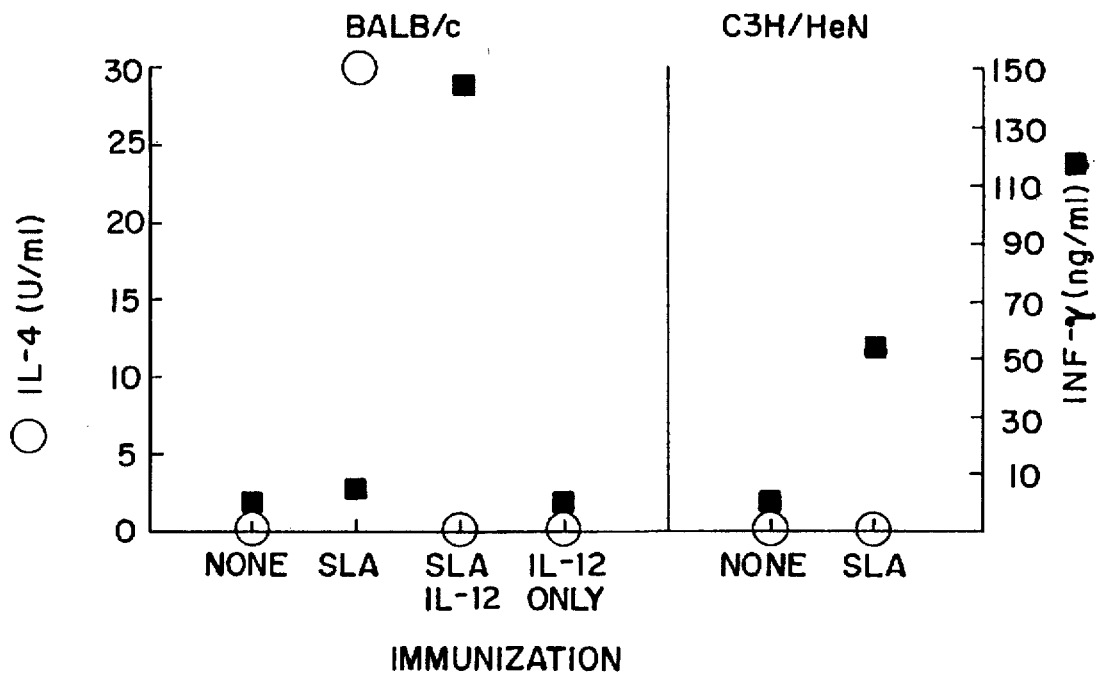
FIG. IA
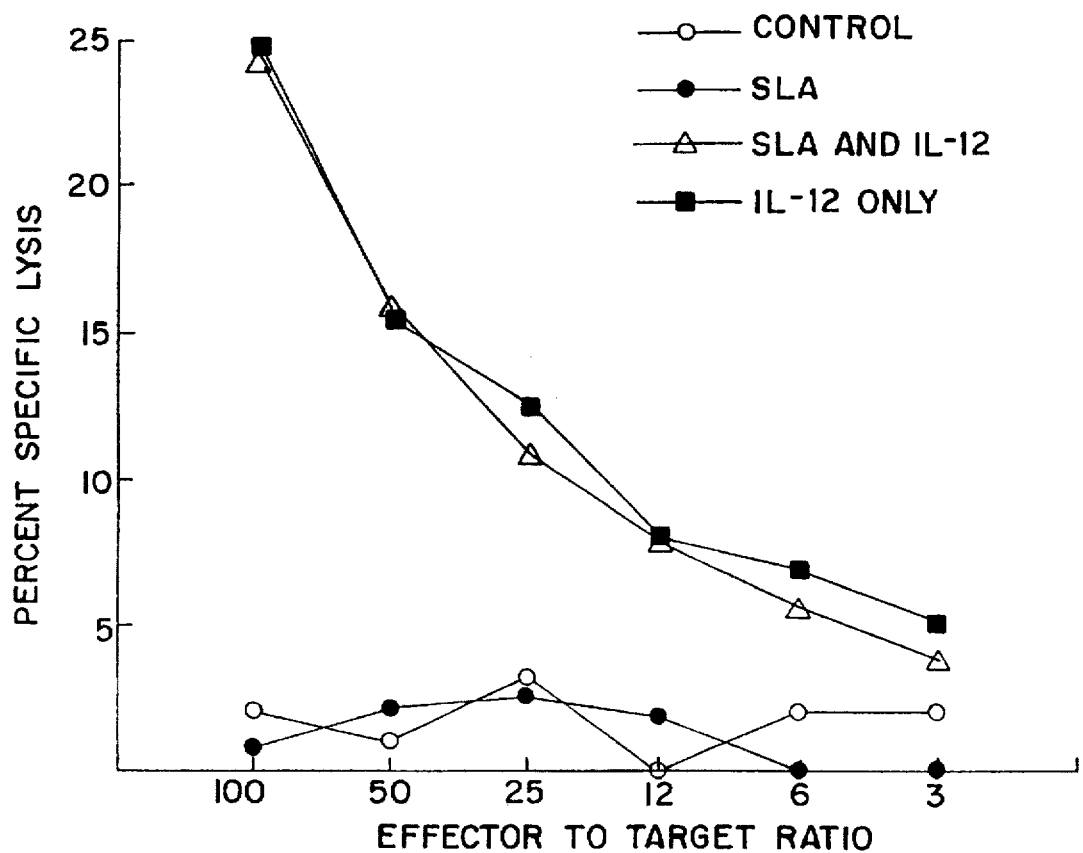
FIG. IB

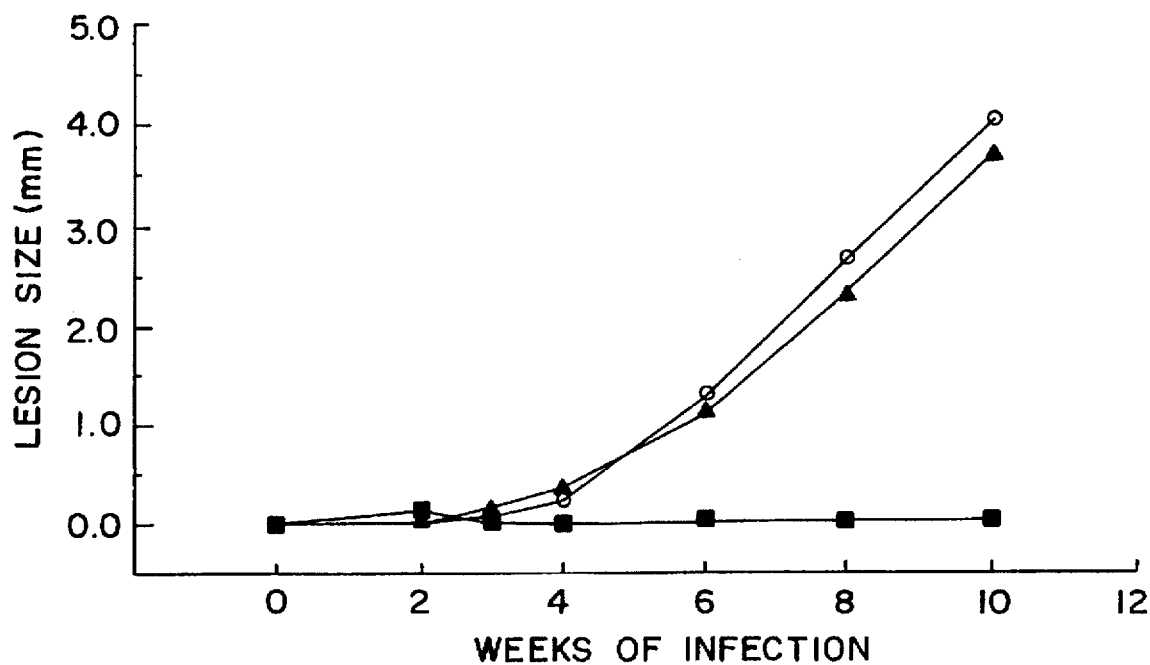
F I G. 3A
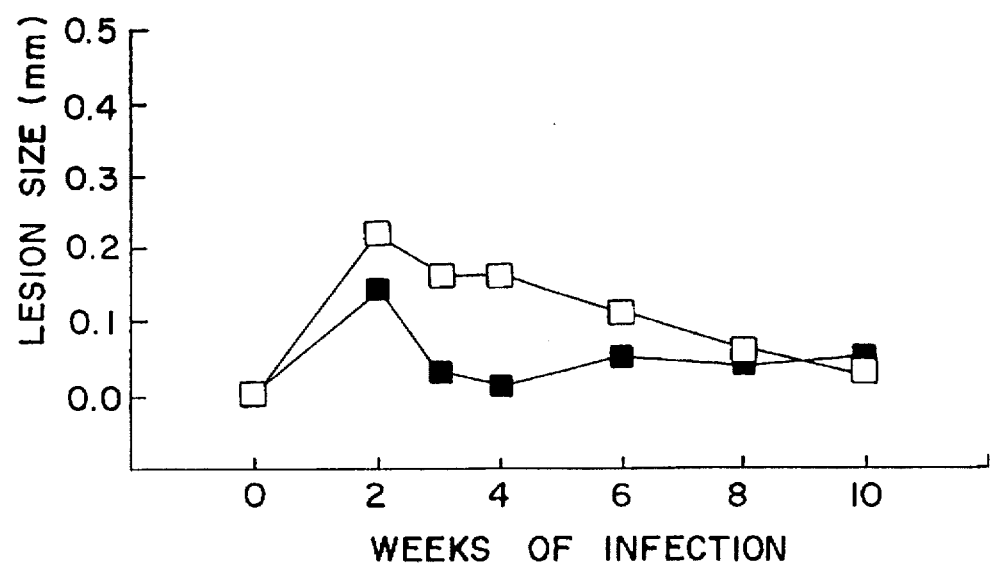
F I G. 3B

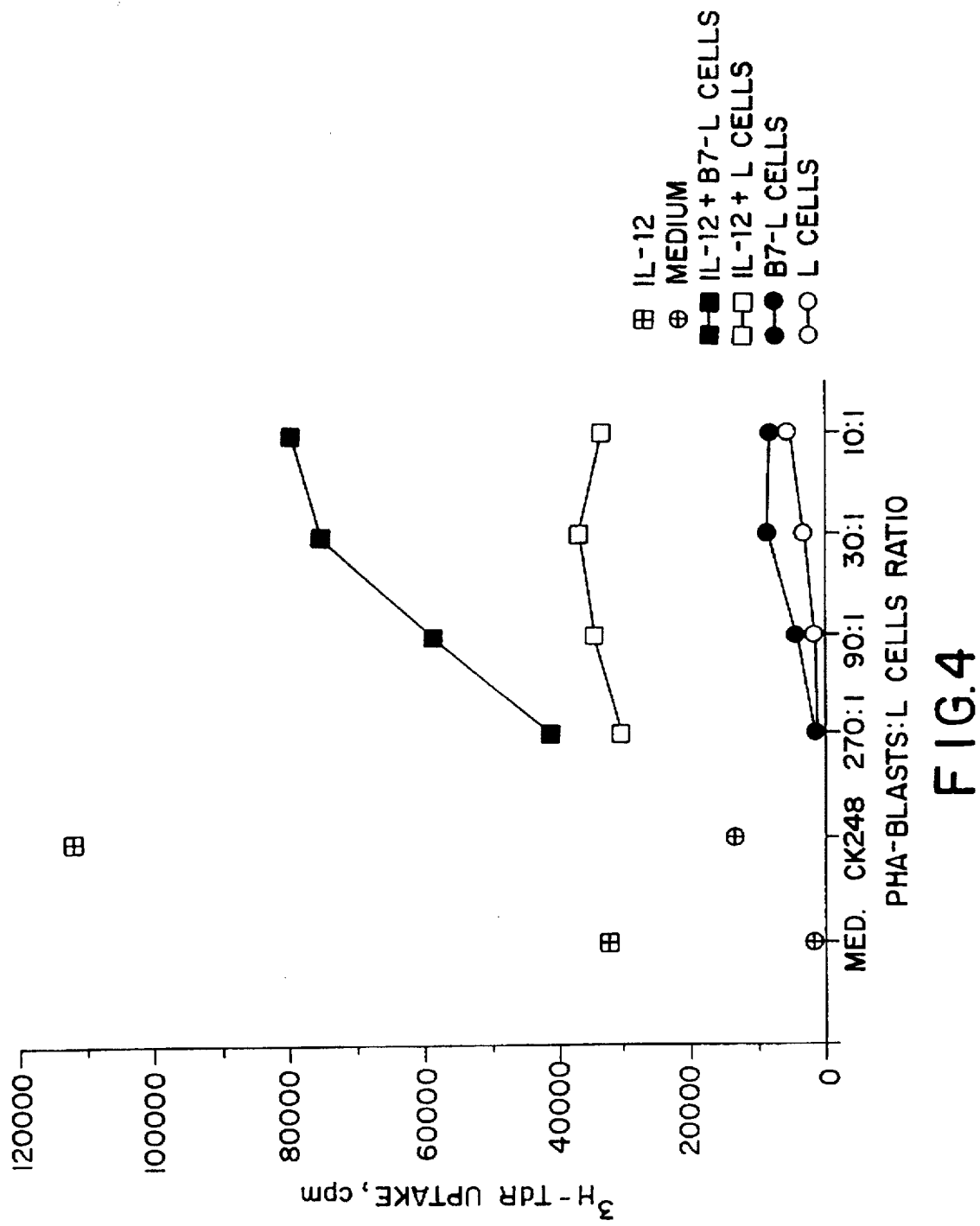

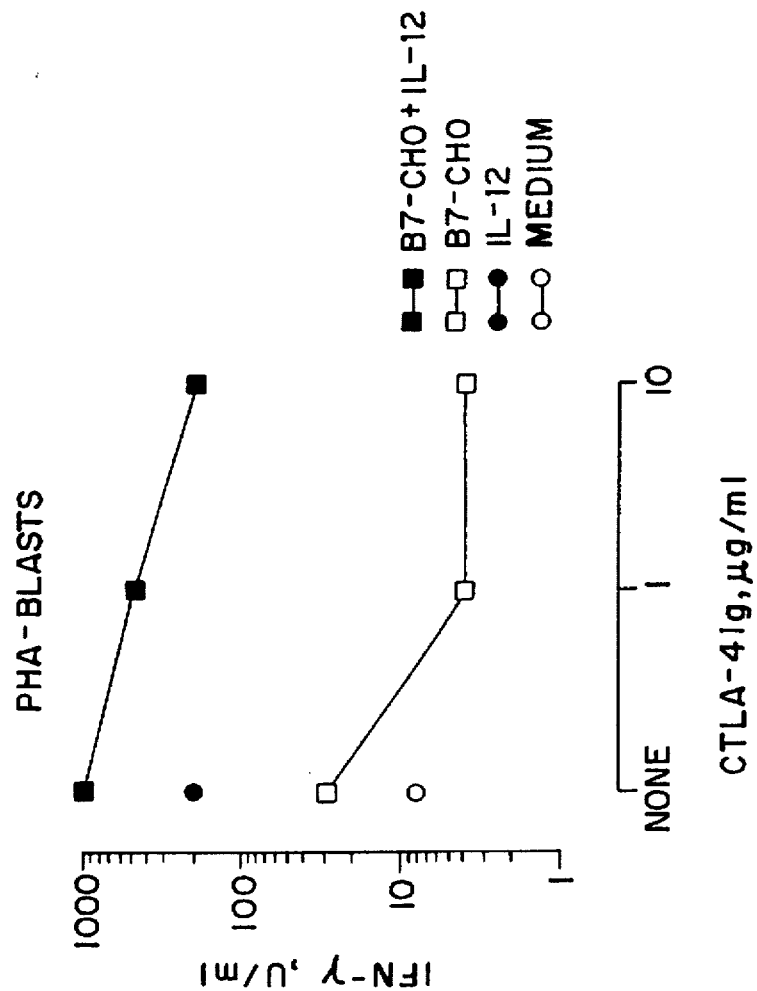
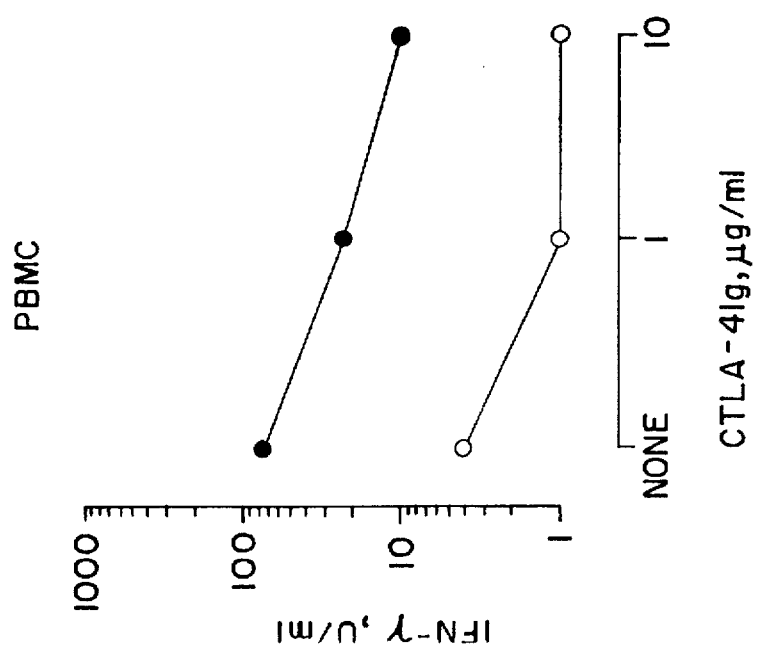

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2362 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 33..1016

( x i ) SEQUENCE DESCRIPTION: SEQ ID NO:1:

```
GAATTCCGTC  GACTCTAGAG  GCCCAGAGCA  AG  ATG  TGT  CAC  CAG  CAG  TTG  GTC         53
                                        Met  Cys  His  Gln  Gln  Leu  Val
                                         1                    5

ATC  TCT  TGG  TTT  TCC  CTG  GTT  TTT  CTG  GCA  TCT  CCC  CTC  GTG  GCC  ATA    101
Ile  Ser  Trp  Phe  Ser  Leu  Val  Phe  Leu  Ala  Ser  Pro  Leu  Val  Ala  Ile
          10                    15                         20

TGG  GAA  CTG  AAG  AAA  GAT  GTT  TAT  GTC  GTA  GAA  TTG  GAT  TGG  TAT  CCG    149
Trp  Glu  Leu  Lys  Lys  Asp  Val  Tyr  Val  Val  Glu  Leu  Asp  Trp  Tyr  Pro
     25                         30                         35

GAT  GCC  CCT  GGA  GAA  ATG  GTG  GTC  CTC  ACC  TGT  GAC  ACC  CCT  GAA  GAA    197
Asp  Ala  Pro  Gly  Glu  Met  Val  Val  Leu  Thr  Cys  Asp  Thr  Pro  Glu  Glu
40                            45                    50                         55

GAT  GGT  ATC  ACC  TGG  ACC  TTG  GAC  CAG  AGC  AGT  GAG  GTC  TTA  GGC  TCT    245
Asp  Gly  Ile  Thr  Trp  Thr  Leu  Asp  Gln  Ser  Ser  Glu  Val  Leu  Gly  Ser
               60                         65                         70

GGC  AAA  ACC  CTG  ACC  ATC  CAA  GTC  AAA  GAG  TTT  GGA  GAT  GCT  GGC  CAG    293
Gly  Lys  Thr  Leu  Thr  Ile  Gln  Val  Lys  Glu  Phe  Gly  Asp  Ala  Gly  Gln
               75                         80                         85
```

| | | | | | | | | | | | | | | | | |
|---|---|---|---|---|---|---|---|---|---|---|---|---|---|---|---|---|
| TAC | ACC | TGT | CAC | AAA | GGA | GGC | GAG | GTT | CTA | AGC | CAT | TCG | CTC | CTG | CTG | 341 |
| Tyr | Thr | Cys | His | Lys | Gly | Gly | Glu | Val | Leu | Ser | His | Ser | Leu | Leu | Leu | |
| | | 90 | | | | | 95 | | | | | 100 | | | | |
| CTT | CAC | AAA | AAG | GAA | GAT | GGA | ATT | TGG | TCC | ACT | GAT | ATT | TTA | AAG | GAC | 389 |
| Leu | His | Lys | Lys | Glu | Asp | Gly | Ile | Trp | Ser | Thr | Asp | Ile | Leu | Lys | Asp | |
| | 105 | | | | | 110 | | | | | 115 | | | | | |
| CAG | AAA | GAA | CCC | AAA | AAT | AAG | ACC | TTT | CTA | AGA | TGC | GAG | GCC | AAG | AAT | 437 |
| Gln | Lys | Glu | Pro | Lys | Asn | Lys | Thr | Phe | Leu | Arg | Cys | Glu | Ala | Lys | Asn | |
| 120 | | | | | 125 | | | | | 130 | | | | | 135 | |
| TAT | TCT | GGA | CGT | TTC | ACC | TGC | TGG | TGG | CTG | ACG | ACA | ATC | AGT | ACT | GAT | 485 |
| Tyr | Ser | Gly | Arg | Phe | Thr | Cys | Trp | Trp | Leu | Thr | Thr | Ile | Ser | Thr | Asp | |
| | | | 140 | | | | | 145 | | | | | 150 | | | |
| TTG | ACA | TTC | AGT | GTC | AAA | AGC | AGC | AGA | GGC | TCT | TCT | GAC | CCC | CAA | GGG | 533 |
| Leu | Thr | Phe | Ser | Val | Lys | Ser | Ser | Arg | Gly | Ser | Ser | Asp | Pro | Gln | Gly | |
| | | | 155 | | | | | 160 | | | | | 165 | | | |
| GTG | ACG | TGC | GGA | GCT | GCT | ACA | CTC | TCT | GCA | GAG | AGA | GTC | AGA | GGG | GAC | 581 |
| Val | Thr | Cys | Gly | Ala | Ala | Thr | Leu | Ser | Ala | Glu | Arg | Val | Arg | Gly | Asp | |
| | | 170 | | | | | 175 | | | | | 180 | | | | |
| AAC | AAG | GAG | TAT | GAG | TAC | TCA | GTG | GAG | TGC | CAG | GAG | GAC | AGT | GCC | TGC | 629 |
| Asn | Lys | Glu | Tyr | Glu | Tyr | Ser | Val | Glu | Cys | Gln | Glu | Asp | Ser | Ala | Cys | |
| | 185 | | | | | 190 | | | | | 195 | | | | | |
| CCA | GCT | GCT | GAG | GAG | AGT | CTG | CCC | ATT | GAG | GTC | ATG | GTG | GAT | GCC | GTT | 677 |
| Pro | Ala | Ala | Glu | Glu | Ser | Leu | Pro | Ile | Glu | Val | Met | Val | Asp | Ala | Val | |
| 200 | | | | | 205 | | | | | 210 | | | | | 215 | |
| CAC | AAG | CTC | AAG | TAT | GAA | AAC | TAC | ACC | AGC | AGC | TTC | TTC | ATC | AGG | GAC | 725 |
| His | Lys | Leu | Lys | Tyr | Glu | Asn | Tyr | Thr | Ser | Ser | Phe | Phe | Ile | Arg | Asp | |
| | | | 220 | | | | | 225 | | | | | 230 | | | |
| ATC | ATC | AAA | CCT | GAC | CCA | CCC | AAG | AAC | TTG | CAG | CTG | AAG | CCA | TTA | AAG | 773 |
| Ile | Ile | Lys | Pro | Asp | Pro | Pro | Lys | Asn | Leu | Gln | Leu | Lys | Pro | Leu | Lys | |
| | | | 235 | | | | | 240 | | | | | 245 | | | |
| AAT | TCT | CGG | CAG | GTG | GAG | GTC | AGC | TGG | GAG | TAC | CCT | GAC | ACC | TGG | AGT | 821 |
| Asn | Ser | Arg | Gln | Val | Glu | Val | Ser | Trp | Glu | Tyr | Pro | Asp | Thr | Trp | Ser | |
| | | 250 | | | | | 255 | | | | | 260 | | | | |
| ACT | CCA | CAT | TCC | TAC | TTC | TCC | CTG | ACA | TTC | TGC | GTT | CAG | GTC | CAG | GGC | 869 |
| Thr | Pro | His | Ser | Tyr | Phe | Ser | Leu | Thr | Phe | Cys | Val | Gln | Val | Gln | Gly | |
| | 265 | | | | | 270 | | | | | 275 | | | | | |
| AAG | AGC | AAG | AGA | GAA | AAG | AAA | GAT | AGA | GTC | TTC | ACG | GAC | AAG | ACC | TCA | 917 |
| Lys | Ser | Lys | Arg | Glu | Lys | Lys | Asp | Arg | Val | Phe | Thr | Asp | Lys | Thr | Ser | |
| 280 | | | | | 285 | | | | | 290 | | | | | 295 | |
| GCC | ACG | GTC | ATC | TGC | CGC | AAA | AAT | GCC | AGC | ATT | AGC | GTG | CGG | GCC | CAG | 965 |
| Ala | Thr | Val | Ile | Cys | Arg | Lys | Asn | Ala | Ser | Ile | Ser | Val | Arg | Ala | Gln | |
| | | | | 300 | | | | | 305 | | | | | 310 | | |
| GAC | CGC | TAC | TAT | AGC | TCA | TCT | TGG | AGC | GAA | TGG | GCA | TCT | GTG | CCC | TGC | 1013 |
| Asp | Arg | Tyr | Tyr | Ser | Ser | Ser | Trp | Ser | Glu | Trp | Ala | Ser | Val | Pro | Cys | |
| | | | 315 | | | | | 320 | | | | | 325 | | | |
| AGT | TAGGTTCTGA | TCCAGGATGA | AAATTTGGAG | GAAAAGTGGA | AGATATTAAG | 1066 |
| Ser | | | | | | |

```
CAAAATGTTT AAAGACACAA CGGAATAGAC CCAAAAAGAT AATTTCTATC TGATTTGCTT    1126

TAAAACGTTT TTTTAGGATC ACAATGATAT CTTTGCTGTA TTTGTATAGT TCGATGCTAA    1186

ATGCTCATTG AAACAATCAG CTAATTTATG TATAGATTTT CCAGCTCTCA AGTTGCCATG    1246

GGCCTTCATG CTATTTAAAT ATTTAAGTAA TTTATGTATT TATTAGTATA TTACTGTTAT    1306

TTAACGTTTG TCTGCCAGGA TGTATGGAAT GTTCATACT  CTTATGACCT GATCCATCAG    1366

GATCAGTCCC TATTATGCAA AATGTGAATT TAATTTTATT TGTACTGACA ACTTTTCAAG    1426

CAAGGCTGCA AGTACATCAG TTTTATGACA ATCAGGAAGA ATGCAGTGTT CTGATACCAG    1486

TGCCATCATA CACTTGTGAT GGATGGGAAC GCAAGAGATA CTTACATGGA AACCTGACAA    1546

TGCAAACCTG TTGAGAAGAT CCAGGAGAAC AAGATGCTAG TTCCCATGTC TGTGAAGACT    1606
```

|   |   |   |   |   |   |   |   |   |   |   |
|---|---|---|---|---|---|---|---|---|---|---|
| TCCTGGAGAT | GGTGTTGATA | AAGCAATTTA | GGGCCACTTA | CACTTCTAAG | CAAGTTTAAT | 1666 |
| CTTTGGATGC | CTGAATTTTA | AAAGGGCTAG | AAAAAAATGA | TTGACCAGCC | TGGGAAACAT | 1726 |
| AACAAGACCC | CGTCTCTACA | AAAAAAATTT | AAAATTAGCC | AGGCGTGGTG | GCTCATGCTT | 1786 |
| GTGGTCCCAG | CTGTTCAGGA | GGATGAGGCA | GGAGGATCTC | TTGAGCCCAG | GAGGTCAAGG | 1846 |
| CTATGGTGAG | CCGTGATTGT | GCCACTGCAT | ACCAGCCTAG | GTGACAGAAT | GAGACCCTGT | 1906 |
| CTCAAAAAAA | AAAATGATTG | AAATTAAAAT | TCAGCTTTAG | CTTCCATGGC | AGTCCTCACC | 1966 |
| CCCACCTCTC | TAAAAGACAC | AGGAGGATGA | CACAGAAACA | CCGTAAGTGT | CTGGAAGGCA | 2026 |
| AAAAGATCTT | AAGATTCAAG | AGAGAGGACA | AGTAGTTATG | GCTAAGGACA | TGAAATTGTC | 2086 |
| AGAATGGCAG | GTGGCTTCTT | AACAGCCATG | TGAGAAGCAG | ACAGATGCAA | AGAAAATCTG | 2146 |
| GAATCCCTTT | CTCATTAGCA | TGAATGAACC | TGATACACAA | TTATGACCAG | AAAATATGGC | 2206 |
| TCCATGAAGG | TGCTACTTTT | AAGTAATGTA | TGTGCGCTCT | GTAAAGTGAT | TACATTTGTT | 2266 |
| TCCTGTTTGT | TTATTTATTT | ATTTATTTTT | GCATTCTGAG | GCTGAACTAA | TAAAAACTCT | 2326 |
| TCTTTGTAAT | CAAAAAAAAA | AAAAAAAAC | TCTAGA |   |   | 2362 |

( 2 ) INFORMATION FOR SEQ ID NO:2:

( i ) SEQUENCE CHARACTERISTICS:
        ( A ) LENGTH: 328 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Cys His Gln Gln Leu Val Ile Ser Trp Phe Ser Leu Val Phe Leu
  1               5                  10                  15

Ala Ser Pro Leu Val Ala Ile Trp Glu Leu Lys Lys Asp Val Tyr Val
                 20                  25                  30

Val Glu Leu Asp Trp Tyr Pro Asp Ala Pro Gly Glu Met Val Val Leu
             35                  40                  45

Thr Cys Asp Thr Pro Glu Glu Asp Gly Ile Thr Trp Thr Leu Asp Gln
 50                  55                  60

Ser Ser Glu Val Leu Gly Ser Gly Lys Thr Leu Thr Ile Gln Val Lys
 65                  70                  75                  80

Glu Phe Gly Asp Ala Gly Gln Tyr Thr Cys His Lys Gly Gly Glu Val
                 85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
            195                 200                 205

Glu Val Met Val Asp Ala Val His Lys Leu Lys Tyr Glu Asn Tyr Thr
    210                 215                 220
```

```
Ser  Ser  Phe  Phe  Ile  Arg  Asp  Ile  Ile  Lys  Pro  Asp  Pro  Pro  Lys  Asn
225                           230                      235                      240

Leu  Gln  Leu  Lys  Pro  Leu  Lys  Asn  Ser  Arg  Gln  Val  Glu  Val  Ser  Trp
                    245                      250                      255

Glu  Tyr  Pro  Asp  Thr  Trp  Ser  Thr  Pro  His  Ser  Tyr  Phe  Ser  Leu  Thr
                    260                      265                      270

Phe  Cys  Val  Gln  Val  Gln  Gly  Lys  Ser  Lys  Arg  Glu  Lys  Lys  Asp  Arg
               275                      280                      285

Val  Phe  Thr  Asp  Lys  Thr  Ser  Ala  Thr  Val  Ile  Cys  Arg  Lys  Asn  Ala
     290                      295                      300

Ser  Ile  Ser  Val  Arg  Ala  Gln  Asp  Arg  Tyr  Tyr  Ser  Ser  Ser  Trp  Ser
305                      310                      315                      320

Glu  Trp  Ala  Ser  Val  Pro  Cys  Ser
                    325
```

( 2 ) INFORMATION FOR SEQ ID NO:3:

( i ) SEQUENCE CHARACTERISTICS:
        ( A ) LENGTH: 1364 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 101..859

( x i ) SEQUENCE DESCRIPTION: SEQ ID NO:3:

```
GTCACCGAGA  AGCTGATGTA  GAGAGAGACA  CAGAAGGAGA  CAGAAAGCAA  GAGACCAGAG                60

TCCCGGGAAA  GTCCTGCCGC  GCCTCGGGAC  AATTATAAAA  ATG  TGG  CCC  CCT  GGG              115
                                                 Met  Trp  Pro  Pro  Gly
                                                  1                     5

TCA  GCC  TCC  CAG  CCA  CCG  CCC  TCA  CCT  GCC  GCG  GCC  ACA  GGT  CTG  CAT       163
Ser  Ala  Ser  Gln  Pro  Pro  Pro  Ser  Pro  Ala  Ala  Ala  Thr  Gly  Leu  His
               10                       15                      20

CCA  GCG  GCT  CGC  CCT  GTG  TCC  CTG  CAG  TGC  CGG  CTC  AGC  ATG  TGT  CCA       211
Pro  Ala  Ala  Arg  Pro  Val  Ser  Leu  Gln  Cys  Arg  Leu  Ser  Met  Cys  Pro
               25                       30                      35

GCG  CGC  AGC  CTC  CTC  CTT  GTG  GCT  ACC  CTG  GTC  CTC  CTG  GAC  CAC  CTC       259
Ala  Arg  Ser  Leu  Leu  Leu  Val  Ala  Thr  Leu  Val  Leu  Leu  Asp  His  Leu
          40                       45                      50

AGT  TTG  GCC  AGA  AAC  CTC  CCC  GTG  GCC  ACT  CCA  GAC  CCA  GGA  ATG  TTC       307
Ser  Leu  Ala  Arg  Asn  Leu  Pro  Val  Ala  Thr  Pro  Asp  Pro  Gly  Met  Phe
     55                       60                      65

CCA  TGC  CTT  CAC  CAC  TCC  CAA  AAC  CTG  CTG  AGG  GCC  GTC  AGC  AAC  ATG       355
Pro  Cys  Leu  His  His  Ser  Gln  Asn  Leu  Leu  Arg  Ala  Val  Ser  Asn  Met
70                       75                      80                      85

CTC  CAG  AAG  GCC  AGA  CAA  ACT  CTA  GAA  TTT  TAC  CCT  TGC  ACT  TCT  GAA       403
Leu  Gln  Lys  Ala  Arg  Gln  Thr  Leu  Glu  Phe  Tyr  Pro  Cys  Thr  Ser  Glu
                    90                       95                     100

GAG  ATT  GAT  CAT  GAA  GAT  ATC  ACA  AAA  GAT  AAA  ACC  AGC  ACA  GTG  GAG       451
Glu  Ile  Asp  His  Glu  Asp  Ile  Thr  Lys  Asp  Lys  Thr  Ser  Thr  Val  Glu
               105                      110                     115

GCC  TGT  TTA  CCA  TTG  GAA  TTA  ACC  AAG  AAT  GAG  AGT  TGC  CTA  AAT  TCC       499
Ala  Cys  Leu  Pro  Leu  Glu  Leu  Thr  Lys  Asn  Glu  Ser  Cys  Leu  Asn  Ser
          120                      125                     130

AGA  GAG  ACC  TCT  TTC  ATA  ACT  AAT  GGG  AGT  TGC  CTG  GCC  TCC  AGA  AAG       547
Arg  Glu  Thr  Ser  Phe  Ile  Thr  Asn  Gly  Ser  Cys  Leu  Ala  Ser  Arg  Lys
     135                      140                     145
```

| | | | | | | | | | | | | | | | | |
|---|---|---|---|---|---|---|---|---|---|---|---|---|---|---|---|---|
| ACC | TCT | TTT | ATG | ATG | GCC | CTG | TGC | CTT | AGT | AGT | ATT | TAT | GAA | GAC | TTG | 595 |
| Thr | Ser | Phe | Met | Met | Ala | Leu | Cys | Leu | Ser | Ser | Ile | Tyr | Glu | Asp | Leu | |
| 150 | | | | | 155 | | | | 160 | | | | | | 165 | |
| AAG | ATG | TAC | CAG | GTG | GAG | TTC | AAG | ACC | ATG | AAT | GCA | AAG | CTT | CTG | ATG | 643 |
| Lys | Met | Tyr | Gln | Val | Glu | Phe | Lys | Thr | Met | Asn | Ala | Lys | Leu | Leu | Met | |
| | | | 170 | | | | | 175 | | | | | | 180 | | |
| GAT | CCT | AAG | AGG | CAG | ATC | TTT | CTA | GAT | CAA | AAC | ATG | CTG | GCA | GTT | ATT | 691 |
| Asp | Pro | Lys | Arg | Gln | Ile | Phe | Leu | Asp | Gln | Asn | Met | Leu | Ala | Val | Ile | |
| | | | 185 | | | | | 190 | | | | | 195 | | | |
| GAT | GAG | CTG | ATG | CAG | GCC | CTG | AAT | TTC | AAC | AGT | GAG | ACT | GTG | CCA | CAA | 739 |
| Asp | Glu | Leu | Met | Gln | Ala | Leu | Asn | Phe | Asn | Ser | Glu | Thr | Val | Pro | Gln | |
| | | 200 | | | | | 205 | | | | | 210 | | | | |
| AAA | TCC | TCC | CTT | GAA | GAA | CCG | GAT | TTT | TAT | AAA | ACT | AAA | ATC | AAG | CTC | 787 |
| Lys | Ser | Ser | Leu | Glu | Glu | Pro | Asp | Phe | Tyr | Lys | Thr | Lys | Ile | Lys | Leu | |
| | 215 | | | | | 220 | | | | | 225 | | | | | |
| TGC | ATA | CTT | CTT | CAT | GCT | TTC | AGA | ATT | CGG | GCA | GTG | ACT | ATT | GAT | AGA | 835 |
| Cys | Ile | Leu | Leu | His | Ala | Phe | Arg | Ile | Arg | Ala | Val | Thr | Ile | Asp | Arg | |
| 230 | | | | | 235 | | | | | 240 | | | | | 245 | |
| GTG | ATG | AGC | TAT | CTG | AAT | GCT | TCC | TAAAAAAGCG | | AGGTCCCTCC | | AAACCGTTGT | | | | 889 |
| Val | Met | Ser | Tyr | Leu | Asn | Ala | Ser | | | | | | | | | |
| | | | | 250 | | | | | | | | | | | | |

| | | | |
|---|---|---|---|
| CATTTTTATA AAACTTTGAA ATGAGGAAAC TTTGATAGGA TGTGGATTAA GAACTAGGGA | | | 949 |
| GGGGGAAAGA AGGATGGGAC TATTACATCC ACATGATACC TCTGATCAAG TATTTTTGAC | | | 1009 |
| ATTTACTGTG GATAAATTGT TTTTAAGTTT TCATGAATGA ATTGCTAAGA AGGGAAAATA | | | 1069 |
| TCCATCCTGA AGGTGTTTTT CATTCACTTT AATAGAAGGG CAAATATTTA TAAGCTATTT | | | 1129 |
| CTGTACCAAA GTGTTTGTGG AAACAAACAT GTAAGCATAA CTTATTTTAA AATATTTATT | | | 1189 |
| TATATAACTT GGTAATCATG AAAGCATCTG AGCTAACTTA TATTTATTTA TGTTATATTT | | | 1249 |
| ATTAAATTAT TCATCAAGTG TATTTGAAAA ATATTTTTAA GTGTTCTAAA AATAAAAGTA | | | 1309 |
| TTGAATTAAA AAAAAAAAAA AAAAAAAAAA AAAAAAAAAA AAAAAAAAAA AAAAA | | | 1364 |

( 2 ) INFORMATION FOR SEQ ID NO:4:

( i ) SEQUENCE CHARACTERISTICS:
        ( A ) LENGTH: 253 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | |
|---|---|---|---|---|---|---|---|---|---|---|---|---|---|
| Met | Trp | Pro | Pro | Gly | Ser | Ala | Ser | Gln | Pro | Pro | Ser | Pro | Ala | Ala |
| 1 | | | | 5 | | | | | 10 | | | | 15 | |
| Ala | Thr | Gly | Leu | His | Pro | Ala | Ala | Arg | Pro | Val | Ser | Leu | Gln | Cys | Arg |
| | | | 20 | | | | | 25 | | | | | 30 | | |
| Leu | Ser | Met | Cys | Pro | Ala | Arg | Ser | Leu | Leu | Leu | Val | Ala | Thr | Leu | Val |
| | | 35 | | | | | 40 | | | | | 45 | | | |
| Leu | Leu | Asp | His | Leu | Ser | Leu | Ala | Arg | Asn | Leu | Pro | Val | Ala | Thr | Pro |
| | 50 | | | | | 55 | | | | | 60 | | | | |
| Asp | Pro | Gly | Met | Phe | Pro | Cys | Leu | His | His | Ser | Gln | Asn | Leu | Leu | Arg |
| 65 | | | | | 70 | | | | 75 | | | | | 80 | |
| Ala | Val | Ser | Asn | Met | Leu | Gln | Lys | Ala | Arg | Gln | Thr | Leu | Glu | Phe | Tyr |
| | | | | 85 | | | | | 90 | | | | | 95 | |
| Pro | Cys | Thr | Ser | Glu | Glu | Ile | Asp | His | Glu | Asp | Ile | Thr | Lys | Asp | Lys |
| | | | 100 | | | | | 105 | | | | | 110 | | |
| Thr | Ser | Thr | Val | Glu | Ala | Cys | Leu | Pro | Leu | Glu | Leu | Thr | Lys | Asn | Glu |
| | | 115 | | | | | 120 | | | | | 125 | | | |

-continued

| | | | | | | | | | | | | | | |
|---|---|---|---|---|---|---|---|---|---|---|---|---|---|---|
| Ser | Cys 130 | Leu | Asn | Ser | Arg | Glu 135 | Thr | Ser | Phe | Ile | Thr 140 | Asn | Gly | Ser | Cys |
| Leu 145 | Ala | Ser | Arg | Lys | Thr 150 | Ser | Phe | Met | Met | Ala 155 | Leu | Cys | Leu | Ser | Ser 160 |
| Ile | Tyr | Glu | Asp | Leu 165 | Lys | Met | Tyr | Gln | Val 170 | Glu | Phe | Lys | Thr | Met 175 | Asn |
| Ala | Lys | Leu | Leu 180 | Met | Asp | Pro | Lys | Arg 185 | Gln | Ile | Phe | Leu | Asp 190 | Gln | Asn |
| Met | Leu | Ala 195 | Val | Ile | Asp | Glu | Leu 200 | Met | Gln | Ala | Leu | Asn 205 | Phe | Asn | Ser |
| Glu | Thr 210 | Val | Pro | Gln | Lys | Ser 215 | Ser | Leu | Glu | Glu | Pro 220 | Asp | Phe | Tyr | Lys |
| Thr 225 | Lys | Ile | Lys | Leu | Cys 230 | Ile | Leu | Leu | His | Ala 235 | Phe | Arg | Ile | Arg | Ala 240 |
| Val | Thr | Ile | Asp | Arg 245 | Val | Met | Ser | Tyr | Leu 250 | Asn | Ala | Ser | | | |

COMPOSITIONS AND METHODS FOR USE OF IL-12 AS AN ADJUVANT

This is a divisional of U.S. patent application Ser. No. 08/265,087, filed on Jun. 17, 1994 now U.S. Pat. No. 5,571,515, which is a continuation-in-part of U.S. patent application Ser. No. 08/229,282, filed Apr. 18, 1994.

This invention was made with financial assistance of National Institutes of Health Grant Nos. AL30073, CA20833, CA10815, CA32898, CA40256 and A120846. The United States government has certain rights in this invention.

FIELD OF THE INVENTION

The present invention relates generally to adjuvantation, and to the use of IL-12 as an adjuvant in pharmaceutical compositions, particularly in vaccines against infections requiring enhanced cell mediated immune (CMI) responses for effective protection against infection by a pathogen.

BACKGROUND OF THE INVENTION

The immune system uses many mechanisms for attacking pathogens, but not all of these are activated after immunization. Protective immunity induced by vaccination is dependent on the capacity of the vaccine to elicit the appropriate immune response to either resist, control, or eliminate the pathogen. Depending on the pathogen, this may require a cell-mediated or humoral immune response, which, in turn, is determined by the nature of the T cells that develop after immunization. For example, many bacterial, protozoal and intracellular parasitic and viral infections appear to require a strong cell-mediated immune response for protection, while other pathogens, such as helminths, primarily respond to a humoral, or antibody, response.

The current paradigm of the role of T cells in the particular immune response is that $CD4^+$ T cells can be separated into subsets on the basis of the repertoire of cytokines produced and that the distinct cytokine profile observed in these cells determines their function. This T cell model includes two major subsets: $T_H1$ cells that produce IL-2 and interferon γ (IFN-γ) and mediate cellular immune responses, and $T_H2$ cells that produce IL-4, IL-5, and IL-10 and augment humoral immune responses [T. R. Mosmann et al, *J. Immunol.*, 126:2348 (1986)].

Many vaccine compositions employ adjuvants, that is, substances which enhance the immune response when administered together with an immunogen or antigen. Adjuvants are thought to function in several ways, including by increasing the surface area of antigen, prolonging the retention of the antigen in the body thus allowing time for the lymphoid system to have access to the antigen, slowing the release of antigen, targeting antigen to macrophages, activating macrophages, or otherwise eliciting non-specific activation of the cells of the immune system [see, e.g., H. S. Warren et al, *Annu. Rev. immunol.*, 4:369 (1986)]. Currently, an essential role of adjuvants in vaccines is to direct $CD4^+$ T cell subset differentiation, although how adjuvants perform this function is poorly understood.

The ability of a adjuvant to induce and increase a specific type of immune response and the identification of that ability is thus a key factor in the selection of particular adjuvants for vaccine use against a particular pathogen. Typical adjuvants include water and oil emulsions, e.g., Freund's adjuvant, and chemical compounds such as aluminum hydroxide or alum. At present, alum is the only adjuvant approved in the United States for human vaccines; it has been determined that alum induces the production of $T_H2$ cells.

Many of the most effective adjuvants include bacteria or their products, e.g., microorganisms such as the attenuated strain of *Mycobacterium bovis*, bacillus Calmette-Guerin (BCG); microorganism components, e.g., alum-precipitated diphtheria toxoid, bacterial lipopolysaccharide and endotoxins. However, the role that the bacteria play is ill-defined. Recently, it has been noted that many bacteria or their products, lipopolysaccharide, *Staphylococcus aureus*, *Mycobacterium tuberculosis*, and *C. parvum*, stimulate IL-12 production by macrophages [A. D'Andrea et al, *J. Exp. Med.*, 176:1387 (1992)].

However, despite their immunostimulating properties, many bacterial adjuvants have toxic or other negative effects, particularly in humans. For example, such a large population has been exposed to some of the bacterial adjuvants, like BCG, that there is a danger of eliciting a secondary response with future use as a vaccine adjuvant. Heat-killed bacteria, being non-native to mammalian hosts, also risk causing toxic effects in the host. In fact, the only currently well-accepted adjuvant for human use is the compound, alum.

Thus, there exists a need in the art for additional adjuvants which are useful in stimulating or enhancing the host's immune responses without inducing a toxic effect, and which are suitable for use in pharmaceutical compositions, such as vaccines.

BRIEF SUMMARY OF THE INVENTION

In one aspect the present invention provides a pharmaceutical composition useful as a vaccine comprising an antigen from a pathogenic microorganism and an effective adjuvanting amount of the protein, Interleukin-12 (IL-12), the resulting composition capable of eliciting the vaccinated host's cell-mediated immunity for a protective response to the pathogen. Preferably the pathogen against which the vaccine is directed is an intracellular parasite, such as a virus, bacterium, or protozoan. The pathogen may also be an extracellular parasite, e.g., a helminth or bacterium. The antigen may be a whole cell, a protein, a protein subunit or fragment. Also preferably the IL-12 is recombinant IL-12 or a biologically active fragment thereof.

In another aspect, the invention provides for a composition comprising DNA sequences encoding the antigen from a pathogenic microorganism, a subunit, or a fragment thereof, rather than the protein or peptide itself. These DNA sequences, together with appropriate promoter sequences, may be employed directly ("naked DNA") as an antigen administered with, or close in time to, the IL-12 adjuvant. Alternatively, these DNA sequences may be transduced in alternate vaccine strains of the pathogenic microorganism, and upon expression in vivo may provide the antigen of the vaccine.

In still another aspect, the invention provides for the use of DNA sequences encoding IL-12, a subunit, or a fragment thereof. These DNA sequences, together with appropriate promoter sequences, may be employed directly ("naked DNA") as an adjuvant administered with, or close in time to, the antigen of the pathogenic microorganism. Alternatively, these DNA sequences may be transduced in alternate vaccine strains of the pathogenic microorganism, and upon expression in vivo may adjuvant the vaccine.

In yet a further embodiment, the DNA sequences encoding the antigen, a subunit, or a fragment thereof may be operably linked to, or co-transfected with the DNA sequences encoding IL-12, as subunit, or a fragment thereof.

In another aspect, the invention provides a method for preparing a vaccine composition containing an antigen from a pathogenic microorganism with enhanced ability to elicit the vaccinated host's CMI response against a pathogen or a DNA sequence encoding the antigen by adding to the vaccine composition an effective amount of the protein IL-12, an IL-12 subunit, or a biologically active fragment thereof or alternatively DNA sequences encoding IL-12, a subunit of IL-12, or a fragment thereof.

In still a further aspect the invention provides a method for increasing the ability of a vaccine composition containing an antigen from a pathogen (as protein and/or subunit, 'naked' DNA, or transduced DNA or a biologically active fragment thereof) to elicit the vaccinate's CMI for a protective immune response against the pathogen by administering to the vaccinate either simultaneously with or sequentially to the vaccine composition, an effective adjuvanting amount of IL-12 (as protein and/or subunit, 'naked' DNA, or transduced DNA or a biologically active fragment thereof).

In another aspect, the invention provides a therapeutic composition for the treatment or amelioration of the symptoms of cancer, and a method for adjuvanting a therapeutic cancer "vaccine". A cancer vaccine or therapeutic may comprise an antigen expressed on the surface of a cancer cell. This antigen may be naturally present on the cancer cell. Alternatively, the cancer cell may be manipulated ex vivo and transfected with a selected antigen, which it then expresses when introduced into the patient. An exemplary therapeutic composition described herein can contain the protein B7 (either alone as a protein, biologically active fragment or 'naked' DNA encoding same) or preferably a B7 transfected cancer cell in combination with IL-12 (as protein and/or subunit, 'naked' DNA or transduced DNA or a biologically active fragment thereof). The co-administration of IL-12 with a B7 preparation enhances the T-cell stimulating activity of the B7 preparation.

Other aspects and advantages of the present invention will be apparent upon consideration of the following detailed description of preferred embodiments thereof.

BRIEF DESCRIPTIONS OF THE DRAWINGS

FIG. 1A is a graph providing the results of in vitro gamma interferon (IFN-γ; solid square) and Interleukin-4 (IL-4; open circle) production by lymph node (LN) cells taken from normal BALB/c mice ("none") or mice inoculated subcutaneously three days previously with soluble leishmanial antigen (SLA), SLA+IL-12, or IL-12 alone, as described in Example 1 below. The C3H/HeN mice were used as controls only.

FIG. 1B is a graph plotting effector to target (E:T) ratio against specific lysis (%) which provides the natural killer (NK) cell cytotoxic response of LN cells from BALB/c mice immunized with nothing (control, open circle), SLA (solid circle), SLA+IL-12 (solid triangle) or IL-12 only (solid square) against YAC-1 target cells. The cytokine responses depicted are from one representative experiment out of five, in which the mean IFN-γ levels in mice immunized with SLA and SLA+IL-12 were 4.6±1.1 and 114±20 ng/ml, respectively (P<0.005). In five out of five experiments, IL-12 reduced IL-4 levels to less than 1 U/ml.

FIG. 2A is a graph reporting the results representative of two or more experiments studying cytokine responses (IL-4, open circle; γ-IFN, solid square) of unfractionated or CD4$^+$ T cell enriched popliteal lymph nodes harvested from BALB/c mice 10 days after immunization with SLA alone or SLA+IL-12; none refers to untreated animals. Only the data from cells cultured with SLA (50 μg/ml) are shown since in the absence of antigen there was no response.

FIG. 2B is a graph plotting the results representative of two or more experiments studying the same cytokine responses of FIG. 2A of unfractionated or CD4$^+$ T cell enriched spleen cells harvested from BALB/c mice 10 days after immunization with IL-12 alone, SLA alone, and SLA IL-12; none refers to untreated animals. Additionally, one group of mice was depleted of NK cell activity before immunization with SLA+IL-12 by pretreatment with anti-asialo GM1 (aASGM1) [WAKO, Richmond, Va.], which is an antibody to an antigen found preferentially on NK cells.

FIG. 3A is a graph plotting weeks of infection vs. lesion size for unimmunized BALB/c mice (▲), BALB/c mice immunized with SLA (○) or SLA+IL-12 (■), and normal C3H/HeN mice (□). Each mouse was injected in the left footpad with 1×10$^5$ purified metacyclic L. major promastigates and the course of infection monitored by measurement of lesion size. Each data point represents the mean lesion size of live mice. Differences in lesion size between control or SLA and SLA+IL-12 were significant from week four onward. Similar results were obtained in three experiments.

FIG. 3B is a graph plotting the course of infection in unimmunized C3H/HeN mice as compared with that in BALB/c mice immunized with SLA+IL-12. Immunization and symbols are the same as described for FIG. 3A.

FIG. 4 is a graph plotting cell proliferation vs. PHA-blast:L cells ratio. Medium alone is symbolized by a circle with a plus; IL-12 by a square with a plus; IL-12 and B7-transfected L cells by a solid square; IL-12 and untransfected L cells by an empty square; B7 transfected L cells only by a solid circle; and untransfected L cells by an empty circle.

FIG. 5 is a bar graph charting amount of IFN-γ in U/ml vs. PHA-blast:CHO-cell ratios indicated for IL-12 at concentrations of 1 ng/ml indicated by a clear rectangle, 0.3 ng/ml by a rectangle with slanted lines; and 0.1 ng/ml by a cross-hatched rectangle, or no IL-12 by a solid rectangle.

FIG. 6A is a bar graph charting IFN-γ production vs. inducers in which the PHA blasts are grown. Symbols used are clear rectangle for antibody to CD3; crosshatched rectangle for IL-2; hatched rectangle for IL-12 and solid rectangle for medium. The experiment is described in Example 5, part I.

Figure 2A:
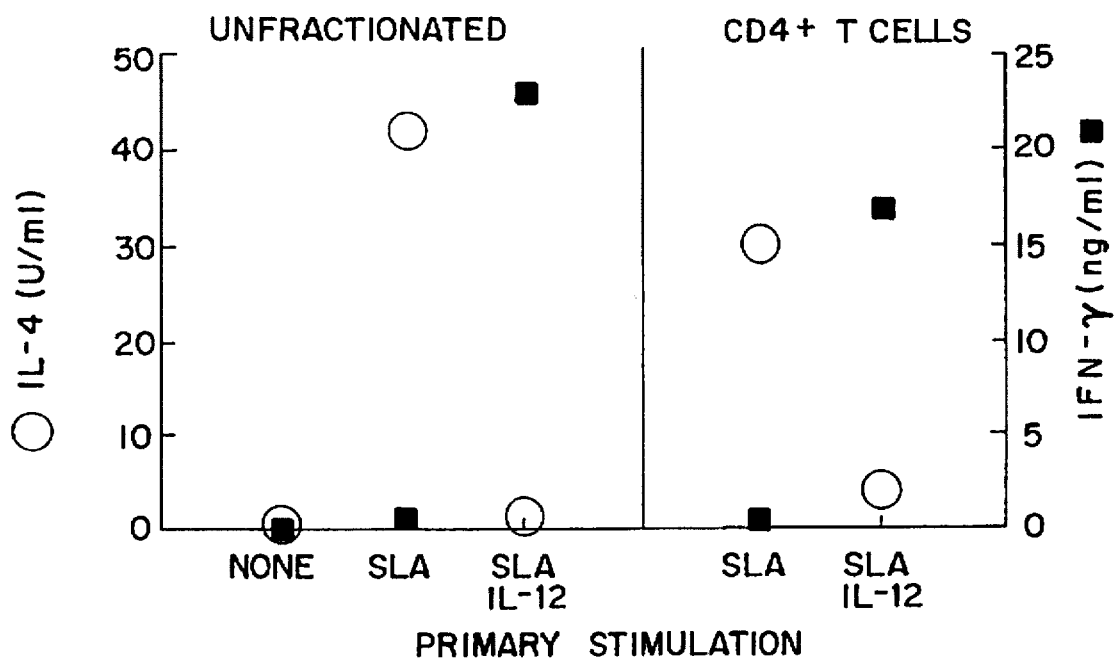

FIG. 7A is a graph plotting IFN-γ production vs. CTLA-41 g concentration in PBMC. Symbols are solid square for IL-12 and B7 transfected CHO cells; clear square for transfected cells only; solid circle for IL-12 only and clear circles for medium only. The experiment is described in Example 5J.

FIG. 7B is a graph plotting IFN-γ production vs. CTLA-41 g concentration in PHA-blasts. All symbols are as in FIG. 7A.

DETAILED DESCRIPTION OF THE INVENTION

The present invention provides novel vaccine compositions and methods of adjuvantation of vaccines intended to provide a protective cell-mediated immune response in vaccinated host mammals against certain pathogens using as an adjuvant, IL-12. Most desirably, the invention is directed to vaccines which rely on enhancing the vaccinated host's cell-mediated immunity, i.e., the elicitation of cytotoxic T lymphocytes (CTLs) and activated phagocytes, to provide protection against infection by the selected pathogen.

The present invention also provides novel therapeutic compositions and methods of adjuvantation intended to provide a synergistic effect with certain therapeutic compositions, particularly so-called "cancer vaccines", which include a selected antigen occurring naturally on a cancer cell or a cancer cell transfected with, and capable of expressing, a selected antigen, e.g., B7. Such compositions may demonstrate an enhanced proliferative effect on T cells and cytokine production thereby. This proliferative effect may exhibit some resistance to chemotherapeutics and thus provide another therapeutic agent and regimen for cancer treatment or in the stimulation of the immune response in the environment of inflamed tissues.

Interleukin-12 (IL-12), originally called natural killer cell stimulatory factor, is a heterodimeric cytokine described, for example, in M. Kobayashi et al, J. Exp. Med., 170:827 (1989). The expression and isolation of IL-12 protein in recombinant host cells is described in detail in International Patent Application WO90/05147, published May 17, 1990 (also European patent application No. 441,900), incorporated by reference herein. The DNA and amino acid sequences of the 30 kd and 40 kd subunits of the heterodimeric human IL-12 are provided in the above recited international application, and are reproduced in the Sequence Listing attached hereto. Research quantities of recombinant human and murine IL-12 are also available from Genetics Institute, inc., Cambridge, Masss. IL-12 has been found to stimulate IFN-γ production by NK cells and T cells [S. H. Chan et al, J. Exp. Med., 173:869 (1991)]. Therapeutic effects of IL-12 administered systemically have been reported [See, e.g., F. P. Heinzel et al, J. Exp. Med., 177:1505 (1993) and J. P. Sypek et al, ibid, p. 1797, among others]. Where it is used throughout the examples, the term IL-12 refers to the heterodimeric protein unless smaller fragments thereof are specifically identified.

As discussed in detail in the examples below, the inventors have discovered a new use for IL-12, including fragments of IL-12 which share the same biological activity of the full-length protein as well as the DNA sequences which encode IL-12 or fragments thereof. IL-12 and biologically active fragments thereof and alternatively the 'naked' or transduced DNA encoding the IL-12 can be employed as an effective adjuvant, particularly for vaccines which require the stimulation of protective cell-mediated immunity against the pathogen.

Diseases requiring CMI stimulation for effective protection may be broadly defined. For example, diseases caused by intracellular or extracellular parasites, certain bacterium, protozoan, heiminths and viruses are most likely to require CMI for protection. Desirable viral vaccines candidates which may be enhanced by adjuvantation with IL-12 include, without limitation, HIV, Hepatitis A, Hepatitis B, Hepatitis C, rabies virus, poliovirus, influenza virus, meningitis virus, measles virus, mumps virus, rubella, pertussis, encephalitis virus, papilloma virus, yellow fever virus, respiratory syncytial virus, parvovirus, chikungunya virus, haemorrhagic fever viruses, Klebsieiia, and Herpes viruses, particularly, varicella, cytomegalovirus and Epstein-Barr virus.

Bacterial vaccines against leprosy and tuberculosis, among others, should also benefit from the use of IL-12 adjuvant. Similarly, vaccines for the induction of protection against parasitic infections such as leishmaniasis and malaria, among others, may also be adjuvanted with IL-12 according to this invention. Still another vaccine which can employ IL-12 adjuvantation is a vaccine against a protozoan, e.g., T. cruzii, or against a helminth, e.g., Schistosoma.

The adjuvanting effect of IL-12 on a vaccine directed against the intracellular parasite causing leishmaniasis in the examples detailed below provides evidence that it is an important component in vaccines against diseases and disease-causing pathogens which require the induction of cell-mediated immunity, e.g., the induction of CTLs and activated phagocytes, for effective protection.

As illustrated in the examples below, the protein IL-12 or a biologically active fragment thereof (or 'naked' DNA sequence encoding IL-12), preferably produced by synthetic or recombinant means, may be used as an effective adjuvant in place of conventional bacterial adjuvants.

When used as an adjuvant for a selected vaccine composition containing an antigen of a pathogenic microorganism, IL-12 is desirably admixed as part of the vaccine composition itself. One of skill in the art of vaccine composition is expected to be able to readily determine suitable amounts of IL-12 to adjuvant particular vaccines. Such amounts will depend upon the pathogen for which the vaccine is designed, the nature of the antigen, the dosage amounts of the antigen as well as the species and physical and medical conditions (e.g., general healthy, weight, etc.) of the vaccinate. As one example, an effective adjuvanting amount of IL-12 protein is desirably between about 0.1 μg to about 0.5 mg of IL-12 protein per about 25 μg of antigen. The adjuvanting amount for any particular vaccine will be readily defined by balancing the efficacy and toxicity of the IL-12 and antigen combination.

When it is administered as part of a vaccine composition, IL-12 is administered by the same route as the vaccinal antigen. Any route of administration may be employed for the administration of this vaccine, e.g., subcutaneous, intraperitoneal, oral, intramuscular, intranasal and the like.

Alternatively, the adjuvanting effect of IL-12 may be employed by administering IL-12 separately from the vaccine composition. When separately administered, the IL-12 is desirably in the presence of a suitable carrier, such as saline and optionally conventional pharmaceutical agents enabling gradual release of the protein. The amount of the IL-12 used in this mode of vaccination is similar to the ranges identified above when IL-12 is part of the vaccine composition. The IL-12 may be administered contemporaneously with the vaccine composition, either simultaneously therewith, or before the vaccine antigen administration. If the IL-12 is administered before the vaccine composition, it is desirable to administer it about one or more days before the vaccine. When IL-12 is administered as a separate component from the vaccine, it is desirably administered by the same route as the vaccinal antigen, e.g., subcutaneous route, or any other route as selected by a physician.

In addition to the administration of the IL-12 protein as an adjuvant, it is also anticipated that nucleic acid sequences encoding IL-12 or a fragment thereof may be used as an adjuvant. The nucleic acid sequences, preferably in the form of DNA, may be delivered to a vaccinate for in vivo expression of the IL-12 protein or peptide. So-called 'naked DNA' may be used to express the IL-12 protein or peptide fragment in vivo in a patient. [See, e.g., J. Cohen, Science, 259:1691–1692 (Mar. 19, 1993); E. Fynan et al, Proc. Natl. Acad. Sci., 90:11478–11482 (Dec. 1993); J. A. Wolff et al, Biotechniques, 11:474–485 (1991) which describe similar uses of 'naked DNA', all incorporated by reference herein].

For example, IL-12 DNA may be incorporated, or transduced, into the microorganism itself, if the whole pathogen itself is to be employed as the vaccinal antigen. Alternatively, IL-12 DNA may be administered as part of the vaccine composition or separately, but contemporaneously with the vaccine antigen, e.g., by injection. Still other modes of delivering IL-12 to the vaccinate in the form of DNA are known to those of skill in the art and may be employed rather than administration of the IL-12 protein, as desired. For example, the IL-12 DNA may be administered as part of a vector or as a cassette containing the IL-12 DNA sequences operatively linked to a promoter sequence. See, e.g., International Patent Application PCT WO94/01139, published Jan. 20, 1994. Briefly, the DNA encoding the IL-12 protein or desired fragment thereof may be inserted into a nucleic acid cassette. This cassette may be engineered to contain, in addition to the IL-12 sequence to be expressed, other optional flanking sequences which enable its insertion into a vector. This cassette may then be inserted into an appropriate DNA vector downstream of a promoter, an mRNA leader sequence, an initiation site and other regulatory sequences capable of directing the replication and expression of that sequence in vivo. This vector permits infection of vaccinate's cells and expression of the IL-12 in vivo.

When IL-12 nucleic acid sequences are used as an adjuvant, these sequences may be operably linked to DNA sequences which encode the antigen. Hence, the vector or cassette, as described above, encoding the IL-12 DNA sequences may additionally include sequences encoding the antigen. Each of these sequences may be operatively linked to the promoter sequence of the vector or cassette. Alternatively, 'naked DNA' encoding the antigen-may be in a separate plasmid. Where present in one or two plasmids, the naked DNA encoding the antigen and/or IL-12, upon introduction into the host cells, permits the infection of vaccinate's cells and expression of both IL-12 and the antigen in vivo.

When IL-12 nucleic acid sequences are employed as the adjuvant either as 'naked DNA' operatively linked to a selected promoter sequence or transduced into a strain of the pathogenic microorganism, rather than the protein itself, the amounts of DNA to be delivered and the routes of delivery may parallel the IL-12 protein amounts and delivery described above and may also be determined readily by one of skill in the art. Similarly the amounts of the antigen as DNA would be selected by one of skill in the art.

Because the induction of IL-12 may be the key component to vaccine efficacy when cell-mediated immunity is required, the use of IL-12 as an adjuvant may be preferable to known adjuvants. For example, unlike adjuvants, such as γ-IFN or IL-2, IL-12 is relatively stable in vivo. Moreover, when γ-IFN was studied by these inventors to adjuvant an L. major vaccine, it was not effective alone as an adjuvant, but required the additional presence of a bacterial adjuvant, C. parvum.

IL-12 as an adjuvant also has an advantage over alum for use in human vaccines. Alum induces $T_H2$ helper cells rather than the $T_H1$ cells induced by IL-12, and thus, alum adjuvanted vaccines may be ineffectual for those pathogenic microorganisms against which a $T_H1$ response is most effective.

Additionally, IL-12 is superior to bacterial adjuvants, such as BCG, which may induce IL-12 as well as other agents or results which may be unanticipated or not controlled. More desirably, IL-12 as an adjuvant should not induce the uncontrolled production of other cytokines, as do bacterial adjuvants which induce IL-12 among a host of other cytokines. Unlike bacterial adjuvants, IL-12 is human in origin and thus unlikely to produce any sensitization. For example in the L. major vaccine model below, vaccination by the subcutaneous route was difficult with other adjuvants, e.g., a combination of γ-IFN and C. parvum, but was successful with IL-12 as adjuvant. As demonstrated with this model, local (sub-cutaneous) injection of IL-12 was not associated with any obvious adverse effects, and there was no appreciable alteration in cell populations within the draining lymph nodes after IL-12 injection.

Thus, it is anticipated that IL-12 will be a highly useful adjuvant for use in human vaccines.

It is further anticipated that IL-12 can be used as an adjuvant in so-called therapeutic vaccines for certain cancers and solid tumors, in a manner similar to that disclosed above for its use as an adjuvant for vaccines containing antigens of a pathogenic microorganism. Particularly where CMI is considered a component of protection against the particular cancer, the use of IL12 as an adjuvant in a cancer vaccine or therapeutic is encompassed by the present invention. Cancer vaccines typically include an antigen expressed on and isolated from a cancer cell or a cancer cell transfected with, and capable of expressing, a selected antigen. For example, any purified tumor antigen may be co-administered with IL-12 as described above for pathogenic vaccines. Identification of relevant cancer antigens will permit the development of such vaccines. Alternatively, other cancer therapeutics are designed using an antigen normally not expressed on a cancer cell. That selected antigen is transfected into the cancer cell and the transfected cell itself, expressing the antigen, is used as the vaccine or therapeutic. Such a vaccine or therapeutic may be co-administered with IL-12 to obtain the adjuvantation effect. The adjuvantation of such vaccines can be accomplished by resort to the above disclosure by one of skill in the art.

The following Examples 1 through 4 illustratively describe a model of the use of recombinant IL-12 in adjuvanting a selected vaccine preparation for *Leishmania major*. Example 5 provides support for the analogous use of IL-12 in adjuvanting the therapeutic effect of a 'cancer vaccine', based on the use of the soluble cell surface glycoprotein B7 [See, S. E. Townsend and James P. Allison, *Science*, 259:368–370 (Jan. 15, 1993)]. These examples are for illustration and do not limit the scope of the present invention.

EXAMPLE 1

Leishmaniasis Model of IL-12 Adjuvant Use

This example demonstrates that IL-12 enhances $T_H1$ cell development in vivo and can replace both *C. parvum* and IFN-γ as a adjuvant in a vaccine against leishmaniasis.

A. The Leishmaniasis Model

The protozoan parasite *Leishmania major* causes leishmaniasis, either a healing or nonhealing cutaneous lesion in mice, depending on the CD4$^+$ $T_H$ cell subset that dominates. Protection requires leishmanial-specific CD4$^+$ T helper ($T_H$) cells, in BALB/c mice. *L. major* infection usually leads to a dominant CD4$^+$ $T_H2$ response, uncontrolled lesion development, metastasis of the parasite, and eventual death of the animal, whereas many other mouse strains (for example, C3H/HeN and C57BL/6) develop a $T_H1$ response, control parasite multiplication, and heal [P. Scott et al, *J. Exp. Med.*, 168:1675 (1988); F. P. Heinzel et al, *ibid*, 169:59 (1989)].

Interferon γ is required for $T_H1$ cell development in this model, since in vivo depletion of IFN-γ before infection abrogates $T_H1$ cell development in resistant C3H/HeN mice, leading to a dominant $T_H2$ response and susceptibility to *L. major* [P. Scott, *J. Immunol.*, 147:3149 (1991)]. However, IFN-γ by itself cannot induce $T_H1$ cell development. For example, as previously reported, when BALB/c mice were immunized subcutaneously with a soluble leishmanial antigen (SLA), inclusion of IFN-γ in the vaccine enhanced protective immunity, but the bacterial adjuvant *Corynebacterium parvum*, was still required for protection, suggesting that other factors may be involved in the differentiation of $T_H1$ cells [P. Scott, cited above].

After subcutaneous injection of either live *L. major* parasites or SLA into BALB/c or C3H/HeN mice there is a rapid response in the draining lymph node (LN), characterized by a three- to five-fold increase in cell number and enhanced cytokine production. in BALB/c mice IL-4 is detected with three days, whereas in C3H/HeN mice the NK cell population expands and produces IFN-γ [P. Scott, cited above; and T. M. Scharton et al, *J. Exp. Med.*, 17.8:567 (1993)].

B. Response to SLA

To determine whether administration of IL-12 alters the initial response to SLA in BALB/c mice, the following experiment was performed. SLA was prepared from *L. major* promastigates as described [P. Scott et el, *J. Immunol.*, 139:221 (1987)]. BALB/c mice were inoculated in the right and left footpad with SLA (25 µg), SLA+IL-12 (0.5 µg), or IL-12 alone, and the popliteal LNs were harvested three days later. C3H/HeN mice were inoculated with SLA alone to provide a comparison of cytokine levels.

Cytokine production by popliteal LN cells taken three days after footpad injection with SLA/SLA+IL-12 was then assessed. LN cells were assayed for cytotoxic potential against $^{51}$Cr-labeled YAC-1 cells in a four-hour Cr-release assay at several effector to target ratios. For cytokine analysis, cells were cultured in 24-well plates at $5 \times 10^6$ per milliliter per well in tissue culture medium [Dulbecco's minimum essential medium with glucose (4.5 mg/ml), 10% fetal bovine serum, 2 mM glutamine, penicillin 6-phosphate (100 U/ml), streptomycin sulfate (100 µg/ml), 25 mM Hepes, and 50 µM 2-mercaptoethanol] with or without SLA (50 µg/ml). Supernatants were harvested at 72 hours and IFN-γ and IL-4 measured by enzyme-linked immunosorbent assay [T. M. Scharton et al, cited above].

As can be seen by reference to FIGS. 1A (only the data from cells cultured with SLA are shown in FIG. 1A) and 1B. LN cells from BALB/c mice injected with SLA produce IL-4 but little IFN-γ, whereas LN cells from C3H/HeN mice produce IFN-γ but little or no IL-4 (FIG. 1A). However, when BALB/c mice were injected with SLA+IL-12, IL-4 production was inhibited (no IL-4 was detected), substantial detectable amounts of IFN-γ, higher than those observed in the resistant C3H/HeN mouse strain, were promoted, and an NK cell response in the draining LN was induced at 72 hours. A similar effect was obtained with several doses of IL-12, including 1, 0.1, and 0.01 µg, although complete ablation of IL-4 was not achieved with the lowest dose [L. C. C. Afonso et al, unpublished data].

The source of the IFN-γ at this early time point has not been determined, although associated with the IFN-γ response was the induction of an NK cell cytotoxic response (FIG. 1B). However, administration of IL-12 alone enhanced NK cell cytotoxic function in the draining LN but failed to stimulate IFN-γ production (see, FIGS. 1A and 1B). This may be due to the capacity of SLA to stimulate the production of other cytokines, such as IL-2, which synergize with IL-12 to enhance IFN-γ production. This finding is compatible with the previous observation that the production of IFN-γ by NK cells during the first three days of *L. major* infection in C3H/HeN mice is dependent on IL-2 produced by CD4$^+$ T cells [T. M. Scharton et al, cited above].

EXAMPLE 2

Induction of $T_H1$ cells

The following experiment was performed to determine whether IL-12 induced the development of a CD4$^+$ $T_H1$ cell population.

BALB/c mice were immunized as described in Example 1. Popliteal LNs and spleens were collected 10 days after the primary in vivo stimulation with SLA or SLA and IL-12, and restimulated in vitro with SLA only. The cytokine profile was then assessed.

CD4$^+$ T cells were cultured at $2 \times 10^6$ per milliliter with irradiated (3300 rad) normal spleen cells ($3 \times 10^6$ milliliter) as antigen-presenting cells. CD4$^+$ T cells were positively selected on a magnetic cell separator (MACS, Miltenyl, Biotec, Sunnyvale, Calif.) as described [T. M. Scharton et al, cited above]. The CD4$^+$ T cell-enriched population contained greater than 98% CD4$^+$ T cells as assessed by cytofluorometric analysis.

To deplete NK cells, mice were treated with a rabbit polyclonal antibody to asialo GM1 |anti-asialoGM1 (ASGM1)] [WAKO, Richmond, Va.] on day 4 (1.5 mg intravenously) and day 0 (350 µg intravenously) [T. M. Scharton et al, cited above].

Figure 2B:
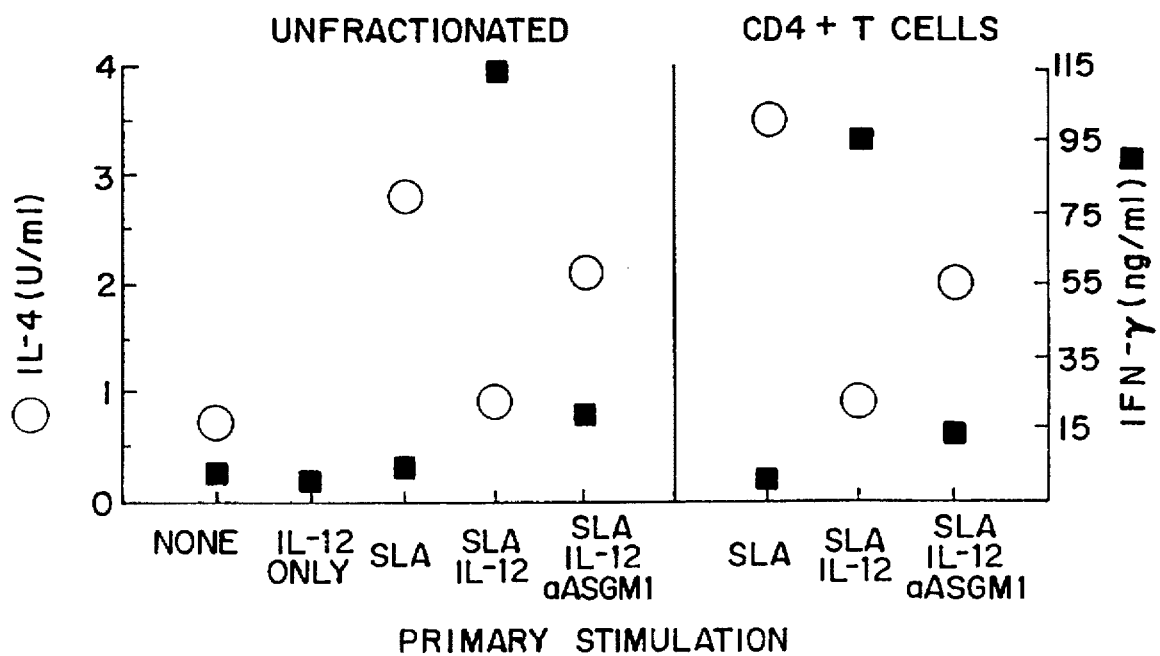

As seen by reference to FIGS. 2A and 2B, IL-12 in the presence of SLA induces differentiation of CD4$^+$ $T_H1$ cells in the LN and the spleen. immunization of the BALB/c mice with SLA primed for a dominant $T_H2$ type response characterized by high IL-4 production. inclusion of IL-12 reversed this pattern, leading to a dominant $T_H1$ response characterized by elevated IFN-γ levels and little, if any, IL-4. A similar response was observed. with both unfractionated lymphocytes and purified CD4$^+$ T cells, indicating that IL-12 was specifically influencing CD4$^+$ $T_H1$ development. In significant contrast, IL-12 administered without antigen had no effect on the capacity of either the LN or the spleen to produce IFN-γ.

EXAMPLE 3

Assessment of $T_H1$ Cell Response

Because an NK cell cytotoxic response was observed with LN cells two days after injection with IL-12 in Example 2 (FIG. 1B), an experiment was conducted to test whether the presence of NK cells contributed to the development of CD4$^+$ $T_H1$ cells after immunization with SLA and IL-12.

Mice were depleted of NK cells by treatment with anti-asialo GM1 before immunization, which completely inhibited NK cell cytotoxic function [L. C. C. Afonso et al, cited above]. A comparison of the response in mice treated with anti-asialo GM1 before immunization with SLA+IL-12, and those not depleted of NK cells, indicated that the presence of NK cells during immunization significantly augmented subsequent $T_H1$ cell development (FIG. 2B). The requirement of NK cells is probably related to their ability to produce IFN-γ, since treatment of mice with anti-IFN-γ monoclonal antibodies also ablated the effects of IL-12. For example, the day 10 spleen cell IFN-γ levels were reported as follows: SLA+IL-12, 58.7 ng/ml; SLA +IL-12 pretreated with anti-IFN-γ, 5.1 ng/ml.

A requirement for the presence of IFN-γ for the in vitro development of $T_H1$ cells in response to IL-12 has been reported [S. E. Macatonia et al. *Int. Immunol.*, 5:1119 (1993)] although in another in vitro system the capacity of IL-12 to initiate $T_H1$ cell development was found to be independent of IFN-γ [R. A. Seder et al. *Proc. Natl. Acad. Sci. USA*, 90:10188 (1993)]. The inventors suggest that NK cells may be one source of IFN-γ in vivo that augments $T_H1$ cell development. Similarly, recent findings in the SCID model with intracellular pathogens indicate that a common pathway for IFN-γ production is through the ability of IL12 to activate NK cells [Co S. Tripp et al. *Proc. Natl. Acad. Sci. USA*, 90:3725 (1993) and R. T. Gazzinelli et al. *ibid*, p. 6115].

EXAMPLE 4

USE OF IL-12 AS ADJUVANT

On the basis of the ability of IL-12 to direct the development of leishmanial-specific CD4$^+$ $T_H1$ cells shown in Example 3 above, an experiment was conducted to demonstrate that IL-12 could act as an adjuvant in a vaccine against *L. major*.

BALB/c mice were immunized in the right footpad with SLA (25 µg) alone or a combination of SLA (25 µg)+IL-12 (1 µg). Ten days later mice were given an intradermal injection in the flank with SLA (10 µg) or SLA+IL-12 (1 µg). Two weeks later mice were challenged in the left footpad with $10^5$ purified metacyclic *L. major* promastigates.

The results of three experiments, reported graphically in FIGS. 3A and 3B, indicate that BALB/c mice immunized with SLA+IL-12 are protected against infection with *L. major*, as measured by the size of the infection-caused lesions. The mean lesion size of mice immunized with SLA+IL-12 at 10 weeks was 0.26±0.50 mm, while unimmunized mice, SLA immunized mice, or mice receiving only IL-12 exhibited lesions of 3 to 5 mm.

One group of mice immunized with SLA+IL-12 was maintained for 20 weeks with no signs of resumption of disease. The lesion size in these animals was as small as that produced in the resistant C3H/HeN mice (FIG. 3B). Cytokine analysis indicated that control mice produced small amounts of IFN-γ and IL-4, whereas mice immunized with SLA+IL-12 produced little IL-4 but amounts of IFN-γ that were comparable to those observed in resistant C3H/HeN mice [L. C. C. Afonso et al. cited above].

Parasite quantitation in lesions of immunized mice weeks after infection demonstrate that lesions from unimmunized BALB/c mice or mice that had been immunized with SLA alone or IL-12 alone contained greater than $10^7$ parasites, whereas BALB/c mice immunized with SLA+IL-12 contained $10^3$ parasites. See, Table 1 below.

TABLE 1

| Mouse strain | Immunization | −log[1] (parasite titer) |
|---|---|---|
| BALB/c | None | 8.1 ± 1.1 |
|  | SLA | 7.7 ± 0.8 |
|  | IL-12 | 7.5 ± 0.3 |
|  | SLA + IL-12 | 3.2 ± 1.9[2] |
| C3H/HeN | None | 1.1 ± 0.1 |

[1]Data represent mean ± SD of at least five animals per group.
[2]p < 0.001 as compared with other BALB/c groups (Student's test).

Thus, this experiment demonstrated that vaccination of BALB/c mice with leishmanial antigens and IL-12 promoted the development of leishmanial-specific CD4$^+$ $T_H1$ cells. These mice were resistant to subsequent infection with *Leishmania major*.

These above reported results demonstrate that IL-12 not only substitutes for conventional bacterial adjuvants, but is likely more efficacious than these conventional adjuvants due to its in vivo stability. Additionally, IL-12 is likely more safe for use in humans due to the fact that is produced recombinantly and purified from any bacterial vector components, and because it is a natural human protein which should not result in any secondary responses or sensitization, as do the bacterial adjuvants.

This adjuvanting effect of IL-12 in conjunction with a vaccine is significantly different than the systemic therapeutic uses previously reported for IL-12. For example, Heinzel et al. and Sypek et al. cited above, administered IL-12 multiple times systemically to BALB/c mice during an *L. major* infection and demonstrated enhanced resistance to the parasite. The enhanced resistance was found only if the IL-12 was administered early in the infection.

This effect is distinct from the adjuvant affects of IL-12 reported in this invention since IL-12 alone does not exhibit any protective effects against subsequent exposure to a pathogen (Table 1). The inventors have discovered that IL-12 in combination with an antigen from a pathogenic microorganism has a protective effect against exposure to the pathogen. This effect is greater than that caused by use of the antigen alone in the vaccine composition or method.

Further, when used as an adjuvant, IL-12 is administered less often and less frequently than systemic therapeutic administration of IL-12, and thereby has substantially lower risk of being present in a vaccinate in toxic levels. For example, an advantage of its use as a vaccine adjuvant is that IL-12 will only be administered as part of the original vaccine and as a booster. Thus, IL-12 should not accumulate in sufficient doses within the vaccinated host, particularly a human, to cause any adverse or toxic effects.

EXAMPLE 5

USE OF IL-12 WITH A CANCER VACCINE

As described in S. Townsend, cited above, one design for a cancer vaccine may involve the soluble, cell surface (membrane)-bound glycoprotein, B7, which is expressed on antigen-presenting cells (APC). B7 is a counter receptor which interacts with the CD28 receptor on T cells to mediate adhesion between the APC and T cells and deliver activating signals to the T cells. Townsend and others have described the use of B7, transfected into tumor cells, as a cancer vaccine. That is, tumor cells from a patient may be removed and some of the cells transfected with B7, using conventional genetic engineering techniques. The transfected cells are then re-introduced into the patient by any mode of delivery, but particularly by subcutaneous delivery.

According to the present invention, IL-12 may be co-administered with this cancer vaccine, either as a protein, biologically active fragment thereof, or the nucleic acid sequence encoding the IL-12. It is anticipated that as DNA, IL-12 may be transfected into the same tumor cell as the B7 for co-administration. Other embodiments of this therapeutic composition include a protein composition containing B7 as a protein and IL-12, as described above for the pathogenic antigens.

The following series of experiments demonstrate that IL-12 is useful as a adjuvant for such a cancer therapeutic. More specifically, these experiments show that the stimulatory pathway of B7 and CD28, a homodimeric molecule of 44 kD subunits expressed on most CD4$^+$ and about half of CD8$^+$ human T cells, but not on natural killer cells [see, A. Aruffo et el, *Proc. Natl. Aced. Sci., USA*, 84:8573 (1987)] synergizes with IL-12 in inducing both efficient proliferation and cytokine production in human T cells. Thus, the addition of IL-12 to such a cancer vaccine enhances the therapeutic effect thereof.

A. Materials and Methods

CHO cell-derived rNKSF/IL-12 was provided by Dr. S. Wolf (Genetics Institute, Boston, MA); rIL-2 (10$^7$ U/mg) was provided by the Division of Cancer Treatment (NCI, Bethesda, Md.); and CHO cell-derived hIL-10 (1.5×10$^7$ U/mg), by Dr. K. Moore (DNAX, Palo Alto, Calif.). The following reagents were obtained from commercial sources: PHA (Sigma Chemical Co., St. Louis, Mo.); heat-fixed *Staphylococcus aureus* Cowan strain 1 (Pansorbin, Calbiochem-Behring Corp., La Jolla, Calif.); 12-0-tetradecanoylphorbol 13-acetate (TPA; Sigma Chemical Co.); CsA (Sandoz Forschungsinstitut GmbH, Vienna, Austria).

mAb OKT3-(IgG2a, anti-CD3) and OKM1-(IgG2b, anti-CD11b) producing cells were obtained from American Type Culture Collection (ATCC, Rockville, Md.); CK248 (IgM, anti-CD28 [A. Moretta et al, *J. Exp. Med.*, 162:823 (1985)] and 93 (IgG1, anti-CD25) were kindly provided by Dr. Lorenzo Moretta (Istituto Nazionale per la Ricerca sul Cancro, Genova, Italy); 1.12 (IgG2a, anti-HLA-DR) by Dr. Roberto Accolla (University of Verona, Italy); B52.1 (IgM, anti-CD14) [B. Perussia et al, *Blood*, 59:382 (1982)] was produced in our laboratory. The mAb 9.3 (IgG2a, anti-CD28 [J. Hansen et al, *Immunogenetics*, 10:247 (1980)] was donated by Drs. J. Hansen (Fred Hutchinson Cancer Center, Seattle, Wash.); mAb B7.4 (IgG, anti-B7) and mAb CD28.1, CD28.2, CD28.3, CD28.5, 15E8 (IgG1, anti-CD28) [J. Nunes et al, *Int. Immunol.*, *5*:311 (1992)] were obtained through the participation in the 5th International Conference on Human Leucocyte Differentiation Antigens. The specificity of all the anti-CD28 antibodies used was assigned at the Conference Workshop and confirmed in our laboratory by reactivity in immunofluorescence with CD28-transfected J32 cell line, but not with the CD28-negative parental cell lines. In immunofluorescence, mAb 9.3 inhibits the binding of mAb CK248 to CD28$^+$ T cells. Anti-IL-2 polyclonal goat antiserum was prepared in our laboratory and, at 1:200 dilution, completely neutralizes the activity of ≧100 U/ml of IL-2. CTLA-4Ig [P. S. Linsley et al, *J. Exp. Med.*, 174:561 (1991)] and B7-transfected CHO cells [P. S. Linsley et al, *J. Exp. Med.*, 173:721 (1991)]were kindly provided by Dr. Peter S. Linsley (Bristol-Meyers Squibb Pharmaceutical Research Institute, Seattle, Wash.); B7-transfected L cells [E. E. Murphy et al, *J. Exp. Med.*, in press (1993)] by Dr. Lewis Lanier (DNAX Research Institute, Palo Alto, Calif.).

B. Cytokine Assays.

Radioimmunoassays (RIA) for human IFN-γ and human tumor necrosis factor-α (TNF-α) were performed as described [M. Murphy et al, *J. Exp. Med.*, 164:263 (1986) and M. C. Cuturi et al, *J. Exp. Med.*, 165:1581 (1987)] using mAbs B133.1/B133.5 and B154.9/B154.7, respectively. Granulocyte-macrophage colony-stimulating factor (GM-CSF) was measured by a newly developed double determinant RIA using antibody C9.1 bound to plastic as capture antibody and antibody C16.3 as $^{125}$I-labeled detection antibody according to the same protocol previously described for IFNγ and TNF-α RIA [M. Murphy et al, cited above and M. C. Cuturi et al, cited above]. Recombinant cytokines were used to standardize all assays.

C. Preparation of Human PBMC.

Peripheral blood obtained from healthy donors was anticoagulated with heparin. PBMC were separated on Ficoll-Hypaque (Lymphoprep; Nyegard and Co., Oslo, Norway) density gradient, and lymphocytes (PBL) were obtained after adherence of PBMC to plastic flasks (1 hour, 37° C.). In some experiments, purified preparations of small high density lymphocytes were purified on a discontinuous Percol gradient [T. Timonen et al, *J. Exp. Med.*, .153:569 (1981)]. These preparations were devoid of cycling cells, as determined by propidium iodide staining and flow cytometry analysis, and did not express significant levels of activation markers CD25, CD69, CD71, and 4F2. Approximately two thirds of the CD4$^+$ cells contained in these populations were CD45 RA$^+$, a phenotype attributed to naive T cells. PHA-blasts (>98% activated T cells), as determined by indirect immunofluorescence with anti-leukocyte subset antibodies, were obtained after 5-day culture of PBL in the presence of 5 μg/ml of PHA [S. H. Chan et al, *J. immunol.*, 148:92 (1992) and S. H. Chan et al, *J. Exp. Med.*, 173:869 (1991)]. Cells were cultured in 200 μl RPMI 1640 medium supplemented with 10% heat-inactivated FCS (Irvine Scientific, Santa Ana, Calif.) in 96-well round-bottomed plates (Flow Laboratories, McLean, Va.) with 0.2×10$^6$ cells/well for proliferation and 1×106 cells/well for cytokine production. For detection of thymidine ($^3$H-TdR) uptake, 1 μCi/well of $^3$H-TdR was added to the wells in the last 6 hours of culture; cells were collected on a glass filter and radioactivity measured. All cultures were performed in triplicate.

D. Immunofluorescence Assay

This assay was performed as described [B. Perussia et al, *J. Immunol.*, 130:2133 (1983)]. Briefly, cells were sequentially incubated (30 minutes, 4° C.) with saturating concentrations of antibodies in PBS containing 1% gelatin, 1% human plasma and 0.1% NAN$_3$, washed 3 times and incubated with FITC-conjugated goat F(ab')$_2$ anti-mouse Ig (Cappel Laboratories, Cochranville, Pa.; absorbed to human IgG-Sepharose before use), washed again, and analyzed for fluorescence and light scatter using an Ortho Cytofluorograf 50 H connected to a 2100 Data Handling System (Ortho Instruments, Westwood, Mass.).

E. Synergy between IL-12 and Anti-CD28 antibody.

In a first experiment, it was shown that IL-12 synergizes with anti-CD28 antibody CK248 and IL-2 in inducing proliferation of PHA-biasts in activated and freshly isolated peripheral blood human T cells. Briefly described, PHA-activated blast cell preparations were obtained after 5 days culture of PBL in the presence of 5 μg/ml PHA in order to avoid the background proliferation observed in PHA-induced cells collected at an earlier time of culture. These preparations were incubated for 3 or 6 days with varying concentrations of IL-12 or IL-2 and no antibodies or 0.04% CD28, 0.2% CD28, or 1% CD28 ascites containing the anti-CD28 antibody CK248. $^3$H-TdR uptake was evaluated after a 6-hour pulse at the end of the culture period.

Results of this experiment (not shown) indicated that increasing concentrations of IL-12 induced modest proliferation in PHA-blasts both at day 3 and 6 of culture, whereas IL-2 alone induced efficient proliferation, with a maximum effect observed around 10 ng/ml. The anti-CD28 antibody CK248, in the absence of IL-12 or IL-2, induced proliferation at day 3 when used at a concentration of ascites fluid of 1:500 or higher. Proliferation at day 6 was lower. Addition of antibody CK248 induced a modest synergistic enhancement of IL-2-induced proliferation but a strong synergistic enhancement of IL-12-induced proliferation.

IL-12 in the presence of CK248 was effective at concentrations as low as 5 pg/ml and induced equivalent $^3$H-TdR uptake at concentrations 2 to 3 orders of magnitude lower than those required with IL-2.

Also tested was the ability of anti-CD28-antibody CK248 to synergize with IL-2 and IL-12 in inducing proliferation of freshly isolated PBL. Synergistic effect with IL-12 was observed at day 6, but not at day 3, although a modest enhancement of IL-2-induced proliferation was already observed at day 3. A similar kinetics of proliferation, with maximum $^3$H-TdR uptake at day 6, was also induced by mAb-CD 248 and IL-12 in two experiments using Percoll-separated high density small lymphocytes.

F. Kinetics of Proliferation

Another experiment demonstrated the kinetics of proliferation of PHA blasts in response to IL-2, IL-12, and anti-CD28 antibodies. Briefly described, PHA-blasts were incubated with the anti-CD28 antibody CK248 (ascites 1%), IL-2 (100 ng/ml), or IL-12 (0.5 ng/ml) and $^3$H-TdR uptake was evaluated at 1, 2, 3, 4, and 6 days after a 6-hour pulse.

Results demonstrated that antibody CK248 was found to induce a proliferative effect only early in the culture, whereas the modest proliferation induced with IL-12 was observed from 1 to 6 days and the proliferation induced by IL-2, CK248 and IL-2, or CK248 and IL-12 was maximum at day 6 and declined at later times.

G. Synergy between B7-transfected cells and IL-12 in inducing proliferation of PHA blasts.

PHA blasts were incubated with the anti-CD28 antibody CK248 (ascites 0.2%) or with different numbers of L-cells transfected or not with the B7 antigen in the presence or not of IL-12 (1 ng/ml). $^3$H-TdR uptake (cpm) was evaluated at 3 days after a 6-hour pulse.

Results shown in FIG. 4 are from one experiment representative of three performed and illustrate that a synergistic proliferative effect with IL-12 was observed by stimulating PHA blasts with L cells transfected with the CD28-ligand B7, but not with non-transfected cells.

H. Synergy between anti-CD-28 antibody CK248 and B7-transfected CHO cells with IL-12 in inducing IFN-γ production from PHA blasts.

Figure 5:
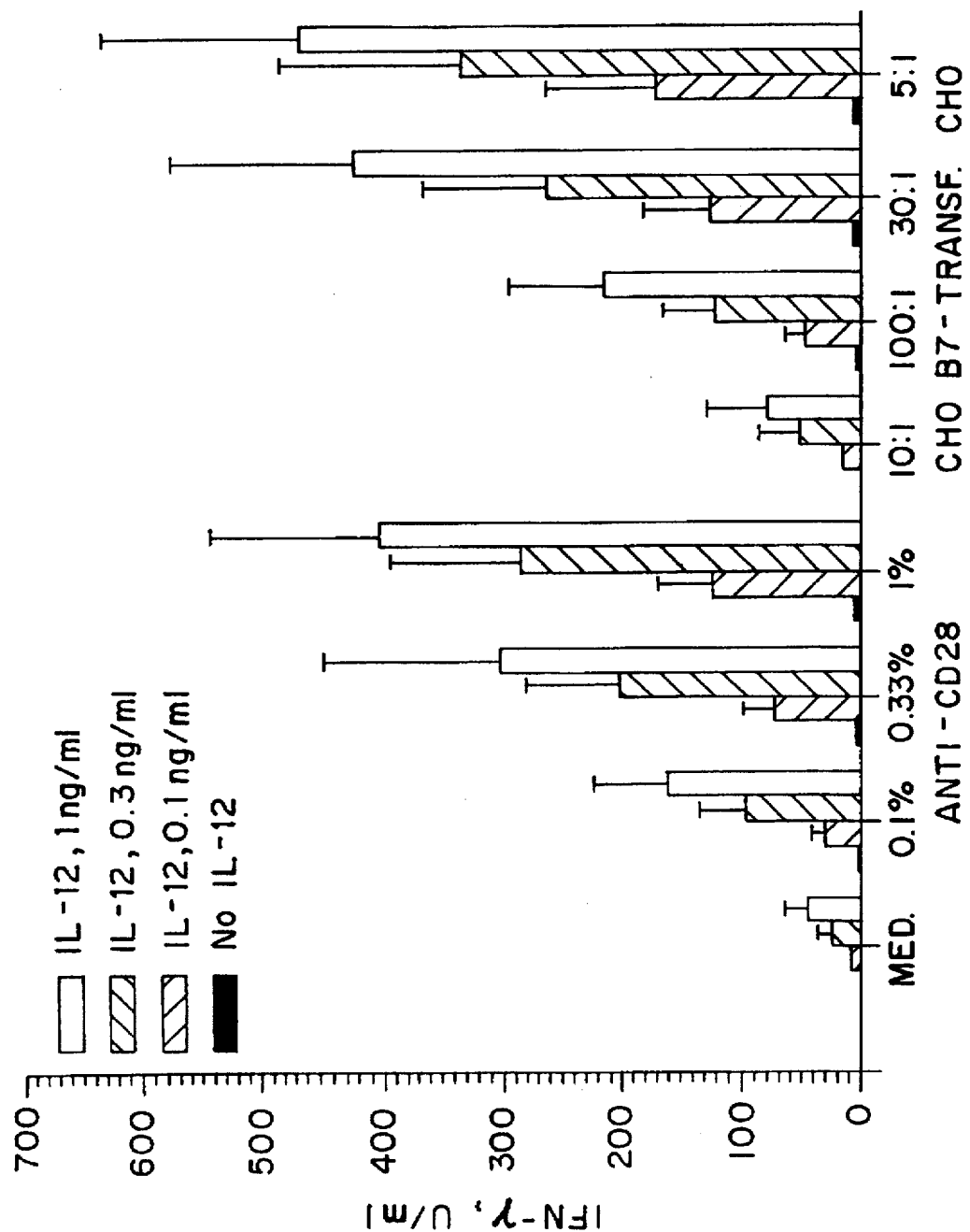

Briefly described, PHA blasts were cultured for 8 hours in the presence of medium or increasing concentrations of IL-12 and the dilutions of ascites of 1 ng/ml, 0.3 ng/ml or 0.1 ng/ml containing the anti-CD28 mAB CK248, parental CHO cells or B7 transfected CHO cells at the PHA blast:CHO cell ratios indicated in FIG. 5. At the end of the culture, cell free supernatant fluids were collected and IFN-γ assayed by the RIA described above in paragraph B.

The results illustrated in FIG. 5 are mean±S.E. of 4 experiments. IL-12 synergizes with stimulation of CD28 by antibodies or by its ligand B7 in inducing production of IFN-γ from PHA-blasts. Control parental CHO cells or control ascites (not shown) had no significant effect, identical results were obtained with B7-transfected L cells (not shown).

I. Synergy between anti-CD28 antibody CK248 and B7transfected CHO-cells with IL-12 in inducing cytokine (IFN-γ, TNF-α,and GM-CSF) production from PHA-blasts.

Briefly described, PHA-blasts were cultured for 18 hours in the presence of medium or in the presence of anti-CD28 mAb CK248 (ascites 1:100), parental CHO cells, B7-transfected CHO cells (ratio PHA-blast:CHO-cells, 10:1). As indicated by the differently shaded columns in FIGS. 6A through 6C, cultures were also stimulated in the presence of IL-12 (1 ng/ml), IL-2 (100 ng/ml), or plastic-bound anti-CD3 OKT3 mAb (5 µg/ml). For comparison, combinations of these three stimuli with IL-12 and IL-2 (final concentrations 1 ng/ml and 100 ng/ml, respectively) are shown in the two rightmost groups of bars in each figure.

Figure 6A:
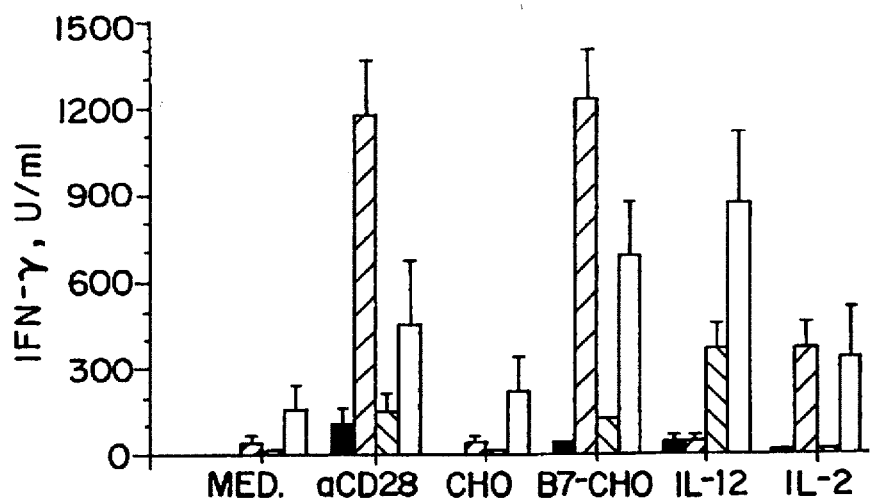
FIG. 6B is a bar graph charting TNF-α production vs inducers. Symbols are as for FIG. 6A.
FIG. 6C is a bar graph charting GM-CSF production vs inducers. Symbols are as for FIG. 6A.
Figure 6B:
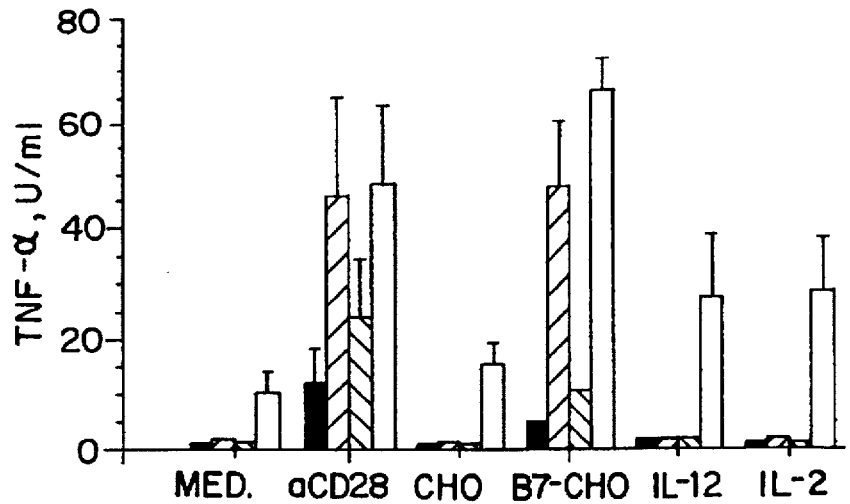
Figure 6C:
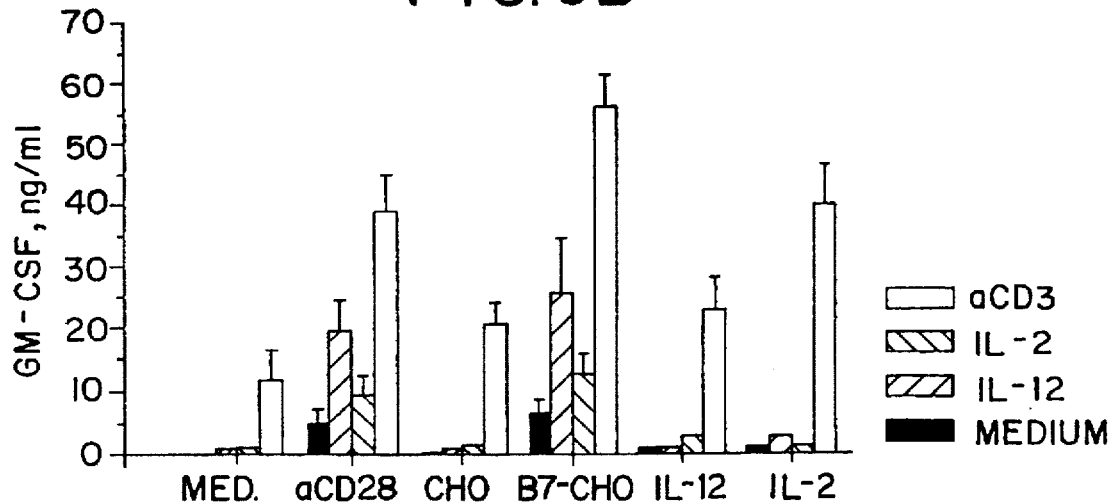

At the end of the 18-hour culture, cell-free supernatant fluids were collected and the three above-identified cytokines measured by RIA described above in paragraph B. Results illustrated in FIGS. 6A through 6C are mean±S.E. of 3 experiments. Anti-CD28 mAb CK248 and B7-transfected CHO cells induced the production by PHA-blasts not only of IFN-γ, but also of TNF-α and GM-CSF, and this effect was enhanced by co-stimulation with IL-12 or plastic-bound anti-CD3 mAb, and, to a lesser extent by IL-2. However, IL-12 was particularly effective in stimulating IFN-γ production as indicated by the fact that anti-CD28 mAb or B7-CHO induced maximal IFN-γ production when in combination with IL-12, whereas they induced TNF-α and GM-CSF more efficiently when combined with plastic-bound anti-CD3. A strong synergy of IL-12 with IL-2 or anti-CD3 was also observed in the induction of IFN-γ production, but not of TNF-α or GM-CSF.

J. Assaying Effect of a B7 ligand on Synergy between IL-12 and B7.

To analyze whether the B7-CD28 interaction plays a role in the IL-12-induced IFN-γ production by PBMC, the ability of the chimeric recombinant soluble B7-ligand CTLA-4Ig to inhibit IFN-γ production was tested. PBL or PHA-blasts were cultured for 18 hours in medium or in the presence of the chimeric protein CTLA-4Ig (concentrations of 0, 1 µg/ml and 10 µg/ml) and stimulated with IL-12 (1 ng/ml) or B7-transfected CHO cells (PHA-blast:CHO cell ratio, 10:1), each component alone or combined. At the end of the culture, cell-free supernatant fluid was collected and IFN-γ assayed by the above-described RIA.

FIGS. 7A and 7B indicate a representative experiment out of 4 performed. CTLA-4Ig efficiently inhibited the production of IFN-γ in PBMC preparations stimulated with IL-12 at the same concentration at which it inhibited the enhancing effect of B7-CHO cells on IFN-γ production by PHA-blasts, stimulated or not with IL-12. Equivalent concentrations of normal human IgG had no effect on IFN-γ production.

The series of experiments summarized above provided results which demonstrate that, in the presence of an appropriate co-stimulus, i.e., signaling through the CD28 receptor induced by B7-transfected cells or certain anti-CD28 antibodies, IL-12 can induce powerful and prolonged proliferation in activated T cells. Not only were the maximal levels of proliferation obtained with IL-12 higher than those induced by IL-2, but IL-12 was maximally effective at concentrations 100- to 1000-fold lower than effective concentrations of IL-2. Moreover, the synergistic proliferation induced by IL-12 and anti-CD28 antibody was also observed with freshly isolated PBL. On both freshly isolated PBL or activated PHA-blasts, anti-CD28 antibodies or B7-transfected cells also synergized with IL-12 in inducing cytokine production.

The synergistic effect of the B7/CD28 costimulatory pathway with IL-12 was observed not only for the proliferation of T cells, but also for the production of cytokines, particularly IFN-γ. The combination of anti-CD28 or B7-transfected cells with IL-12 is the most efficient condition for stimulation of IFN-γ production in freshly isolated or lectin-activated T cells yet described. Other cytokines such as TNF-α and GM-CSF were also induced by a combination of IL-12 and CD28 receptor stimulation.

Because the synergistic effects of CD28 stimulation with IL-12 are observed using the physiologic CD28 ligand B7, it is likely that the response observed with CK248 and other anti-CD28 mAb in the presence of IL-12 reflects the physiologic response of activation of the B7/CD28 costimulatory pathway.

CTLA-4Ig inhibited the production of IFN-γ more than 5-fold in PBMC stimulated with IL-12 alone, suggesting that interaction of T cells with B7 expressed on accessory cells in PBMC has an important role in the responsiveness of fresh peripheral blood cells to IL-12.

In other experiments, it was observed that the ability of IL-12 and anti-CD28 antibodies combined to induce IFN-γ production in PBMC was completely resistant to IL-10.

The ability of monocyte-macrophages and B cells to present a surface counter-receptor and to secrete a soluble cytokine that cooperate with each other in a potent synergistic effect in inducing T cell activation, both in terms of proliferation and cytokine production, is likely to have physiologic significance in vivo during inflammation and immune response.

T cells activated by the B7/CD28 interaction and IL-12 also produce GM-CSF and TNF-α, which may also participate in macrophage activation and enhanced production of IL-12. This effect is likely to amplify both phagocytic cell and T cell activation, e.g., in bacteria-induced inflammation, until negative feedback mechanisms mediated by IL-10 and possibly by IL-4, TGF-β, and other pharmacologic mediators that interrupt this amplifying circle. The synergy between the B7/CD28 pathway and IL-12 demonstrated by the above experiments indicates that IL-12 is a desirable adjuvant for a cancer vaccine or cancer therapeutic, such as that described by Townsend et al, cited above. For example, co-administration to a patient of a tumor cell transfected with B7 and IL-t2 would provide the same type of synergy, e.g., cytokine production and T cell stimulation, preferably directed against the tumor. Thus, such a composition may be employed as a cancer therapeutic, or as a 'vaccine' to prevent reoccurence of a tumor, which has been surgically or otherwise removed.

The above experiments also indicate that the administration of a composition comprising B7 and IL-12 may also be useful as a first line of defense against infections. These results strongly suggest that in the presence of IL-12 and B7 expression on accessory cells, T cells are likely to participate in these non-antigen specific mechanisms. The participation of T cells may be dependent on and follow NK cell activation and production of IFN-γ.

It is therefore likely that the synergistic effect between B7 and IL-12 is important for the activation and differentiation of quiescent T cells as well as for the maintained activation of the effector functions of established mature Th1 clones.

Numerous modifications and variations in practice of this invention are expected to occur to those skilled in the art, and are considered to be encompassed by the following claims.

---

What is claimed is:

1. An antigenic composition comprising a selected antigen from a pathogenic bacteria or virus and an effective adjuvanting amount of Interleukin-12, wherein said Interleukin-12 enhances the cell mediated immune response to said antigen.

2. The composition according to claim 1 wherein said effective amount of IL-12 is about 0.1 µg to about 0.5 mg of IL-12 per 25 µg of antigen.

3. A method for preparing an antigenic composition comprising adding to a composition containing an antigen from a pathogenic bacteria virus, an effective amount of Interleukin-12, said antigenic composition eliciting a stronger immune response in a host than elicited by administration of the antigen alone.

4. A method for increasing the ability of an antigenic composition containing an antigen from a pathogenic bacteria or virus to elicit the host's cell mediated immune response for an immune response against said pathogen or cancer comprising administering to a host simultaneously or sequentially with said antigenic composition, an effective amount of Interleukin-12.

5. A method for increasing the ability of an antigenic composition containing an antigen from a pathogenic bacteria to elicit the host's cell mediated immune response comprising administering to a host an antigenic composition of claim 1.

6. A method for enhancing the immune response elicited by an antigenic composition comprising administering to a host simultaneously or sequentially with said antigenic composition, an effective amount of Interleukin-12.

7. An improved composition useful for eliciting an immune response to a selected pathogen, said composition comprising an antigen from said pathogen, wherein the improvement consists of including interleukin-12 in said composition, and wherein said interleukin-12-containing composition elicits an enhanced immune response to said pathogen.

8. An antigenic composition prepared according to the method of claim 3.

* * * * *

UNITED STATES PATENT AND TRADEMARK OFFICE
CERTIFICATE OF CORRECTION

PATENT NO. : 5,723,127
DATED : March 3, 1998
INVENTOR(S) : Phillip Scott and Giorgio Trinchieri It is certified that error appears in the above-identified patent and that said Letters Patent is hereby corrected as shown below:

Col. 5, line 60, replace "Klebsieiia." with -- Klebsiella, --.

Col. 8, line 20, replace "IL12" with -- IL-12 --.

Col. 9, line 21, replace "17.8:567" with -- 178:567 --.

Col. 11, line 11, replace "IL12" with -- IL-12 --.

Col. 11, line 12, replace "[Co S." with -- [C. S. --.

Col. 11, line 47, insert -- 10 -- after the word "mice" and before the word "weeks".

Col. 13, line 36, delete ":" before "5".

UNITED STATES PATENT AND TRADEMARK OFFICE
CERTIFICATE OF CORRECTION

PATENT NO. : 5,723,127
DATED : March 3, 1998
INVENTOR(S) : Phillip Scott and Giorgio Trinchieri It is certified that error appears in the above-identified patent and that said Letters Patent is hereby corrected as shown below:

Col. 14, line 9, delete "." before "153:569".

Col. 14, line 44, replace "PHA-biasts" with -- PHA-blasts --.

Col. 18, line 4, replace "IL-t2" with -- IL-12 --.

Signed and Sealed this

Twenty-ninth Day of September, 1998

Attest:

BRUCE LEHMAN

Attesting Officer

Commissioner of Patents and Trademarks